US012014831B2

United States Patent
Tang et al.

(10) Patent No.: US 12,014,831 B2
(45) Date of Patent: Jun. 18, 2024

(54) APPROACHES TO REDUCING DIMENSIONALITY OF GENETIC INFORMATION USED FOR MACHINE LEARNING AND SYSTEMS FOR IMPLEMENTING THE SAME

(71) Applicant: AIONCO, Inc., Menlo Park, CA (US)

(72) Inventors: Cheuk Ying Tang, Cupertino, CA (US); Victor Solovyev, San Francisco, CA (US); Gene Lee, Millbrae, CA (US)

(73) Assignee: AIONCO, Inc., Menlo Park, CA (US)

( * ) Notice: Subject to any disclaimer, the term of this patent is extended or adjusted under 35 U.S.C. 154(b) by 0 days.

(21) Appl. No.: 18/073,471

(22) Filed: Dec. 1, 2022

(65) Prior Publication Data

US 2023/0335279 A1   Oct. 19, 2023

Related U.S. Application Data

(60) Provisional application No. 63/285,429, filed on Dec. 2, 2021.

(51) Int. Cl.
  *G16H 50/20* (2018.01)
  *G16B 40/20* (2019.01)
  *G16H 50/70* (2018.01)

(52) U.S. Cl.
  CPC .............. *G16H 50/20* (2018.01); *G16B 40/20* (2019.02); *G16H 50/70* (2018.01)

(58) Field of Classification Search
  CPC ......... G16H 50/20; G16H 50/70; G16B 40/20
  See application file for complete search history.

(56) References Cited

U.S. PATENT DOCUMENTS

| | | |
|---|---|---|
| 7,117,188 B2 | 10/2006 | Guyon et al. |
| 7,542,959 B2 | 6/2009 | Barnhill et al. |
| 8,095,483 B2 | 1/2012 | Weston et al. |
| 10,402,685 B2 | 9/2019 | Guyon et al. |
| 2015/0211068 A1* | 7/2015 | Beim ............. C12Q 1/6883 800/3 |
| 2016/0259880 A1 | 9/2016 | Semenyuk |
| 2020/0118036 A1* | 4/2020 | Karnagel ......... G06N 3/088 |
| 2020/0202975 A1 | 6/2020 | Lee |
| 2021/0313006 A1 | 10/2021 | Gross et al. |
| 2021/0358585 A1 | 11/2021 | Wu et al. |

(Continued)

FOREIGN PATENT DOCUMENTS

| | | |
|---|---|---|
| WO | 2019066421 A2 | 4/2019 |
| WO | 2019232435 A1 | 12/2019 |

OTHER PUBLICATIONS

Sun, Yingshuai et al., "Identification of 12 cancer types through genome deep learning," Scientific Reports 2019, vol. , Article No. 17256, published online: Nov. 21, 2019, 9 pages.

(Continued)

*Primary Examiner* — Jay M. Patel
(74) *Attorney, Agent, or Firm* — Perkins Coie LLP

(57) ABSTRACT

Introduced here is an approach to further refining a set of locations that can serve as inputs to a machine learning algorithm. These locations may refer to unique molecular positions in a reference human genome and/or unique mutations thereof that are relevant in diagnosing cancer. A computing system can determine the diagnostic relevance of each location and then discard some of the less diagnostically relevant locations.

19 Claims, 14 Drawing Sheets

Specification includes a Sequence Listing.

(56) References Cited

U.S. PATENT DOCUMENTS

| | | | |
|---|---|---|---|
| 2023/0050513 A1* | 2/2023 | Morganella | G16B 45/00 |
| 2023/0068937 A1* | 3/2023 | Morganella | G16B 40/20 |
| 2023/0122305 A1* | 4/2023 | Senapathy | G16B 30/10 |
| | | | 435/6.11 |

OTHER PUBLICATIONS

PCT International Search Report and Written Opinion dated Apr. 7, 2023 for PCT/US2022/051578 filed Dec. 1, 2022, Applicant: AIONCO, Inc., ISA/KR, 11 pages.

Mukherjee, S. et al., "Support Vector Machine Classification of Microarray Data," A.I. Memo No. 1677, C.B.C.L Paper No. 182, Massachusetts Institute of Technology Artificial Intelligence Laboratory and Center for Biological and Computational Learning Department of Brain and Cognitive Sciences, Dec. 1999, 11 pages.

Kohavi, Ron et al., "Wrappers for feature subset selection," Elsevier, Artificial Intelligence 97, pp. 273-324, 1997.

Hocking et al., "Selection of the Best Subset in Regression Analysis," Technometrics, vol. 9, No. 4, Nov. 1967, pp. 531-540.

Bradley, Paul Stephen, Mathematical Programming Approaches to Machine Learning and Data Mining, dissertation submitted to the Graduate School of the University of Wisconsin-Madison, 1998, UMI No. 9840134, 181 pages.

Khorshed et al., "Deep Learning for Multi-Tissue Cancer Classification of Gene Expressions (GeneXNet)," IEEE Access, vol. 8, 2020, pp. 90615-90629, published May 6, 2020.

Barton et al., "Whole-exome imputation within UK Biobank powers rare coding variant association and fine-mapping analyses," Analysis, Nature Genetics vol. 53, Aug. 2021, pp. 1260-1269.

Homomorphic Encryption References, Homomorphic Encryption Standardization Webpage, last updated Jun. 23, 2023, people.csail.mit.edu/vinodv/FHE/FHE-refs.html , 5 pages, maintained by Vinod Vaikuntanathan.

* cited by examiner

Examples: 21538

Counter: {1:10578, 0:10960}, where "1" corresponds to cancer while "0" corresponds to healthy.

Features: 46382

Locations: ~160,000

| Cancer | Index | Number of Healthy Samples | Number of Cancerous Samples |
|---|---|---|---|
| ACC | 0 | 271 | 92 |
| BLCA | 1 | 1256 | 419 |
| BRCA | 2 | 3172 | 1072 |
| CESC | 3 | 916 | 307 |
| CHOL | 4 | 172 | 51 |
| COAD | 5 | 1418 | 469 |
| DLBC | 6 | 140 | 37 |
| ESCA | 7 | 506 | 185 |
| GBM | 8 | 1459 | 506 |
| HNSC | 9 | 1679 | 513 |
| KICH | 10 | 141 | 66 |
| KIRC | 11 | 868 | 372 |
| KIRP | 12 | 872 | 294 |
| LAML | 13 | 318 | 162 |
| LGG | 14 | 1537 | 532 |
| LIHC | 15 | 1143 | 379 |
| LUAD | 16 | 1771 | 635 |
| LUSC | 17 | 1504 | 564 |
| MESO | 18 | 246 | 82 |
| OV | 19 | 1454 | 520 |
| PAAD | 20 | 533 | 185 |
| PCPG | 21 | 541 | 184 |
| PRAD | 22 | 1532 | 503 |
| READ | 23 | 495 | 165 |
| SARC | 24 | 755 | 259 |
| SKCM | 25 | 1413 | 472 |
| STAD | 26 | 1366 | 441 |
| TGCT | 27 | 450 | 156 |
| THCA | 28 | 1491 | 507 |
| THYM | 29 | 360 | 123 |
| UCEC | 30 | 1667 | 551 |
| UCS | 31 | 165 | 57 |
| UVM | 32 | 240 | 80 |

FIGURE 10

SEQUENCE LISTING

```
Sequence total quantity: 19
SEQ ID NO: 1            moltype = DNA  length = 34
FEATURE                 Location/Qualifiers
source                  1..34
                        mol_type = genomic DNA
                        organism = Homo sapiens
SEQUENCE: 1
ttggataacc tagaaaaaaa acaaattact ggaa                                   34

SEQ ID NO: 2            moltype = DNA  length = 30
FEATURE                 Location/Qualifiers
source                  1..30
                        mol_type = genomic DNA
                        organism = Homo sapiens
SEQUENCE: 2
ggataaccta gaaaaaaaaa aacaaattac                                        30

SEQ ID NO: 3            moltype = DNA  length = 30
FEATURE                 Location/Qualifiers
source                  1..30
                        mol_type = genomic DNA
                        organism = Homo sapiens
SEQUENCE: 3
ggataaccta gaaaaaaaaa acaaattact                                        30

SEQ ID NO: 4            moltype = DNA  length = 30
FEATURE                 Location/Qualifiers
source                  1..30
                        mol_type = genomic DNA
                        organism = Homo sapiens
SEQUENCE: 4
ggataaccta gaaaaaaaaa caaattactg                                        30

SEQ ID NO: 5            moltype = DNA  length = 30
FEATURE                 Location/Qualifiers
source                  1..30
                        mol_type = genomic DNA
                        organism = Homo sapiens
SEQUENCE: 5
ggataaccta gaaaaaaaac aaattactgg                                        30

SEQ ID NO: 6            moltype = DNA  length = 30
FEATURE                 Location/Qualifiers
source                  1..30
                        mol_type = genomic DNA
                        organism = Homo sapiens
SEQUENCE: 6
ggataaccta gaaaaaaaca aattactgga                                        30
```

| | | |
|---|---|---|
| SEQ ID NO: 7<br>FEATURE<br>source | moltype = DNA   length = 30<br>Location/Qualifiers<br>1..30<br>mol_type = genomic DNA<br>organism = Homo sapiens | |
| SEQUENCE: 7<br>ggataaccta gaaaaaacaa attactggaa | | 30 |
| SEQ ID NO: 8<br>FEATURE<br>source | moltype = DNA   length = 30<br>Location/Qualifiers<br>1..30<br>mol_type = genomic DNA<br>organism = Homo sapiens | |
| SEQUENCE: 8<br>ggataaccta gaaaaacaaa ttactggaaa | | 30 |
| SEQ ID NO: 9<br>FEATURE<br>source | moltype = DNA   length = 17<br>Location/Qualifiers<br>1..17<br>mol_type = genomic DNA<br>organism = Homo sapiens | |
| SEQUENCE: 9<br>atcatcatca tcatcat | | 17 |
| SEQ ID NO: 10<br>FEATURE<br>source<br><br>variation<br>SEQUENCE: 10 | moltype = DNA   length = 24<br>Location/Qualifiers<br>1..24<br>mol_type = other DNA<br>organism = synthetic construct<br>4..19 | |
| acttgaatca tcatcatcct ccta | | 24 |
| SEQ ID NO: 11<br>FEATURE<br>source<br><br>variation<br>SEQUENCE: 11 | moltype = DNA   length = 24<br>Location/Qualifiers<br>1..24<br>mol_type = other DNA<br>organism = synthetic construct<br>5..20 | |
| acttgaatca tcatcatcct ccta | | 24 |
| SEQ ID NO: 12<br>FEATURE<br>source<br><br>S_region<br>SEQUENCE: 12 | moltype = DNA   length = 24<br>Location/Qualifiers<br>1..24<br>mol_type = other DNA<br>organism = synthetic construct<br>6..21 | |
| acttgaatca tcatcatcct ccta | | 24 |
| SEQ ID NO: 13<br>FEATURE<br>source | moltype = DNA   length = 26<br>Location/Qualifiers<br>1..26<br>mol_type = other DNA<br>organism = synthetic construct | |
| SEQUENCE: 13<br>cgtagctgaa aaaaaaacgt acgtag | | 26 |
| SEQ ID NO: 14<br>FEATURE<br>source | moltype = DNA   length = 25<br>Location/Qualifiers<br>1..25<br>mol_type = other DNA<br>organism = synthetic construct | |
| SEQUENCE: 14<br>cgtagctgaa aaaaaacgta cgtag | | 25 |
| SEQ ID NO: 15<br>FEATURE<br>source | moltype = DNA   length = 24<br>Location/Qualifiers<br>1..24<br>mol_type = other DNA<br>organism = synthetic construct | |
| SEQUENCE: 15<br>cgtagctgaa aaaaacgtac gtag | | 24 |
| SEQ ID NO: 16<br>FEATURE<br>source | moltype = DNA   length = 23<br>Location/Qualifiers<br>1..23 | |

```
                        mol_type = other DNA
                        organism = synthetic construct
SEQUENCE: 16
cgtagctgaa aaaacgtacg tag                                              23

SEQ ID NO: 17          moltype = DNA   length = 22
FEATURE                Location/Qualifiers
source                 1..22
                       mol_type = other DNA
                       organism = synthetic construct
SEQUENCE: 17
cgtagctgaa aaacgtacgt ag                                               22

SEQ ID NO: 18          moltype = DNA   length = 13
FEATURE                Location/Qualifiers
source                 1..13
                       mol_type = genomic DNA
                       organism = Homo sapiens
SEQUENCE: 18
ttggataacc tag                                                         13

SEQ ID NO: 19          moltype = DNA   length = 23
FEATURE                Location/Qualifiers
source                 1..23
                       mol_type = other DNA
                       organism = synthetic construct
SEQUENCE: 19
nnnatcatca tcatcatcat nnn                                              23
```

APPROACHES TO REDUCING DIMENSIONALITY OF GENETIC INFORMATION USED FOR MACHINE LEARNING AND SYSTEMS FOR IMPLEMENTING THE SAME

CROSS-REFERENCE TO RELATED APPLICATIONS

This application claims priority to U.S. Provisional Application No. 63/285,429, titled "Feature Selection for Artificial Intelligence-Based Detection of Cancer Through Analysis of Genetic Information" and filed on Dec. 2, 2021, which is incorporated by reference herein in its entirety.

REFERENCE TO SEQUENCE LISTING

This application contains an ST.26 compliant Sequence Listing, which is submitted concurrently in xml format via EFS-Web or Patent Center and is hereby incorporated by reference in its entirety. The .xml copy, created on Jun. 27, 2023, is named 145289.8002.US01 Sequence Listing.xml and is 17.9 KB in size.

TECHNICAL FIELD

Various implementations concern computer programs and associated computer-implemented techniques for processing sequenced information, such as text-based representations of genetic information, for training of machine learning models.

BACKGROUND

Genes are pieces of deoxyribonucleic acid (DNA) inside cells that indicate how to make the proteins that the human body needs to function. At a high level, DNA serves as the genetic "blueprint" that governs operation of each cell. Genes can not only affect inherited traits that are passed from a parent to a child but can also affect whether a person is likely to develop diseases like cancer. Changes in genes—also called "mutations"—can play an important role in the physiological conditions of the human body, such as in the development of cancer. Accordingly, genetic testing may be leveraged to detect such physiological conditions or likely onsets thereof.

The term "genetic testing" may be used to refer to the process by which the genes or portions of genes of a person are examined to identify mutations. There are many types of genetic tests, and new genetic tests are being developed at a rapid pace. While genetic testing can be employed in various contexts, it may be used to detect mutations that are known to be associated with cancer.

Genetic testing could also be employed as a means for addressing or treating the physiological condition. For example, after a person has been diagnosed with cancer, a healthcare professional may examine a sample of cells to look for changes in the genes to track the progression of the cancer, the efficacy of the treatment, etc. These changes may be indicative of the health of the person (and, more specifically, progression or regression of the cancer). Insights derived through genetic testing may provide information on the prognosis, for example, by indicating whether treatment has been helpful in addressing the mutation.

Implementing computing technologies for the genetic testing may yield valuable insights. For example, artificial intelligence (AI) and machine learning (ML) may be leveraged to analyze DNA information for detecting and/or addressing cancers or potential onset of cancers. However, the magnitude of the DNA information, large number of potential mutations, and large number of samples—among other factors—often negatively impact the effectiveness, accuracy, and practicality in leveraging such computing technologies for the genetic testing.

BRIEF DESCRIPTION OF THE DRAWINGS

FIG. 10 includes a table that illustrates how the number of locations at which to search can quickly expand as the number of samples (and thus, features) increases.

Figure 1A:
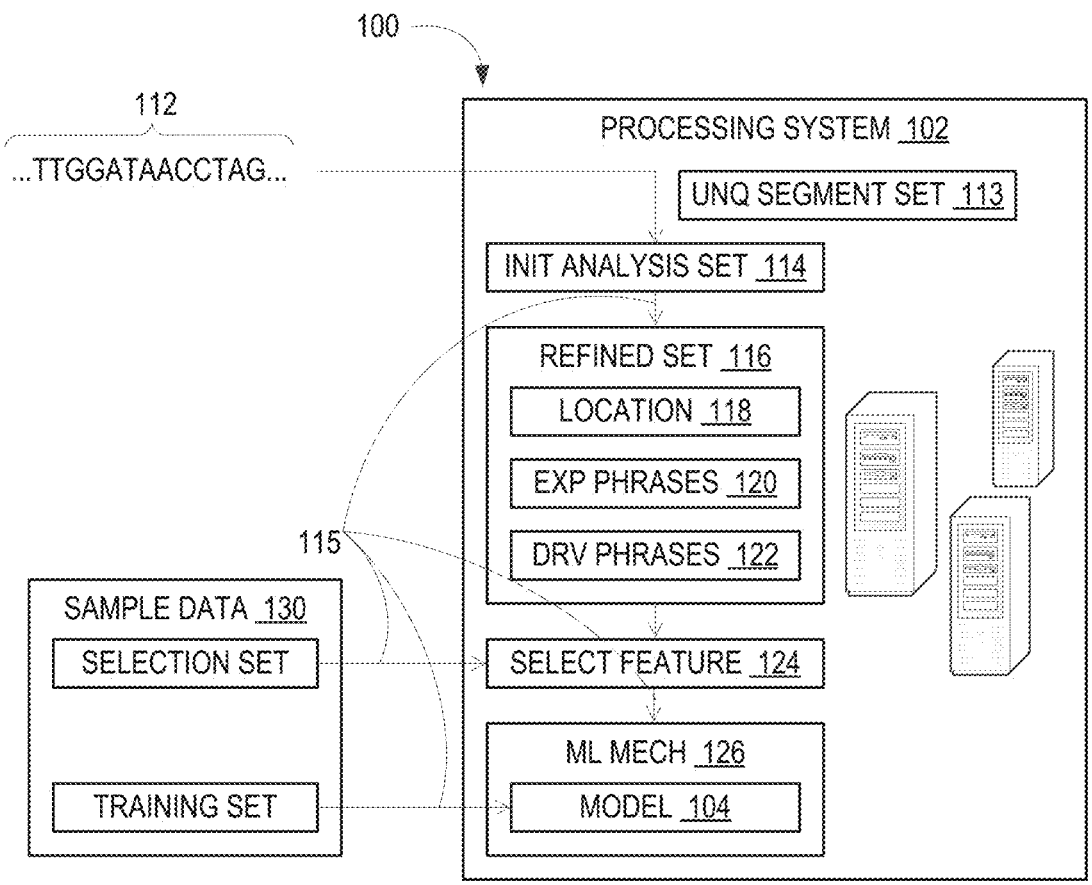
FIGS. 1A (SEQ ID NO: 18) and 1B show example operating environments of a computing system including a genetic information processing system in accordance with one or more implementations of the present technology.

Various features of the technology described herein will become more apparent to those skilled in the art from a study of the Detailed Description in conjunction with the drawings. Various implementations are depicted in the drawings for the purpose of illustration. However, those skilled in the art will recognize that alternative implementations may be employed without departing from the principles of the

DETAILED DESCRIPTION

Genetic testing may be beneficial for diagnosing and treating cancer. For example, identifying mutations that are indicative of cancer can help (1) healthcare professionals make appropriate decisions, (2) researchers direct their investigations, and (3) developers design better therapies, particularly through precision medicine. However, discovering these mutations tends to be difficult, especially as the number of cancers of interest (and thus, corresponding data) increases. Note that the term "mutation," as used herein, may be used to refer to any change in a DNA sequence. Mutations may not only occur in genes but also intergenic regions and non-coding regions.

While computer-aided detection (CADe) processing systems and computer-aided diagnostic (CADx) processing systems may be used to analyze data obtained through genetic testing, conventional approaches still face several drawbacks due to the overwhelming number of computations required for such analysis. For example, conventional systems may identify a number of molecular positions (e.g., target analysis locations)—and combinations of those molecular positions—that may be inefficient, ineffective, inaccurate, or otherwise impractical to process. Moreover, such deficiencies become even more problematic when a conventional system is tasked with reviewing the genetic information of tens, hundreds, or thousands of patients. In other words, even if a conventional system is able to comprehensively analyze the genetic information of a single patient, reviewing the genetic information of tens, hundreds, or thousands of patients during actual deployment becomes impractical due to processing delays and inaccuracies. Further, tasking a conventional system with reviewing the genetic information of tens, hundreds, or thousands of patients may simply be infeasible due to the computational resources that would be necessary.

Introduced here is an approach that can be implemented by a computing system to predict disease onset and/or diagnose disease presence in an improved manner. Implementations of the present technology can include the computing system processing the genetic information as relatively simple (e.g., smaller) computer-readable data, such as text strings (simpler in comparison to, for example, digital images). Using textual representations of genetic information, the computing device can identify specific text patterns, such as unique segments of repeated characters (e.g., tandem repeats (TRs) corresponding to sequences of two or more DNA bases that are repeated numerous times in a head-to-tail manner on a chromosome), phrases surrounding the unique segments, and derivations thereof that are indicative of mutations, used to analyze nucleic acid sequences (or simply "sequences"). In some implementations, the computing system can focus on the unique phrases and/or derivations thereof in characterizing and/or recognizing one or more types of cancer. In some implementations, the computing system can select features from the phrases or derivations and may ignore other portions of the larger textual representation of the sequence, thereby reducing the overall computations needed for developing, training, and/or applying an ML model (or simply "model") or other AI mechanism. While implementation of the approach may result in improvements across different aspects of mutation discovery, there are several notable improvements worth mentioning.

Advantageously, the approach allows models to be trained (and diagnoses to be predicted by those trained models) in a more time- and resource-efficient manner as the number of features considered by the computing system may be reduced (e.g., from tens of thousands of nucleotide locations to several thousand nucleotide locations). For a given type of cancer, the computing system can reduce a first feature set (also called an "expanded feature set") that is discovered through examination of training of genetic information through ML, so as to identify the most important nucleotide locations from a diagnostic perspective without significantly harming the accuracy in identifying mutations that are indicative of the given cancer type. Through reduction of the first feature set, the computing system may produce a second feature set (also called a "reduced feature set") that can be used to train an ML model.

In some implementations, the computing system can include and/or utilize a mutation analysis mechanism that identifies a set of unique portions in the DNA of the human genome and related mutations that correspond to development/onset of certain types of cancer. The computing system can identify the set of unique portions and mutations (e.g., text strings having a length of k) based on the TRs. The computing system may use a refinement mechanism to further process or filter the set of unique portions and mutations. For example, the computing system can use the refinement mechanism to remove duplicate entries, overlapping entries, comparison-based errors, unqualified data, physiology-based noise parameters, and the like within the set. Through the additional refinement, the computing system can further reduce the total number of computations required to analyze and process the genetic information (e.g., in developing and/or implementing the ML model). Moreover, the refinement mechanism can provide reduced errors caused by duplicate computations, excessive computations, insufficient or inconsistent sample sizes, poor data quality, and/or the like.

Implementations may be described in the context of instructions that are executable by a computing system for the purpose of illustration. However, those skilled in the art will recognize that aspects of the technology described herein could be implemented via hardware or firmware instead of, or in addition to, software. As an example, a computer program that is representative of a software-implemented genetic information processing platform (or simply "processing platform") designed to process genetic information may be executed by the processor of a computing system. This computer program may interface, directly or indirectly, with hardware, firmware, or other software implemented on the computing system. Moreover, this computer program may interface, directly or indirectly, with computing devices that are communicatively connected to the system. One example of a computing device is a network-accessible storage medium that is managed by a healthcare entity (e.g., a hospital system or diagnostic testing facility).

Overview of Genetic Information Processing System

Figure 1B:
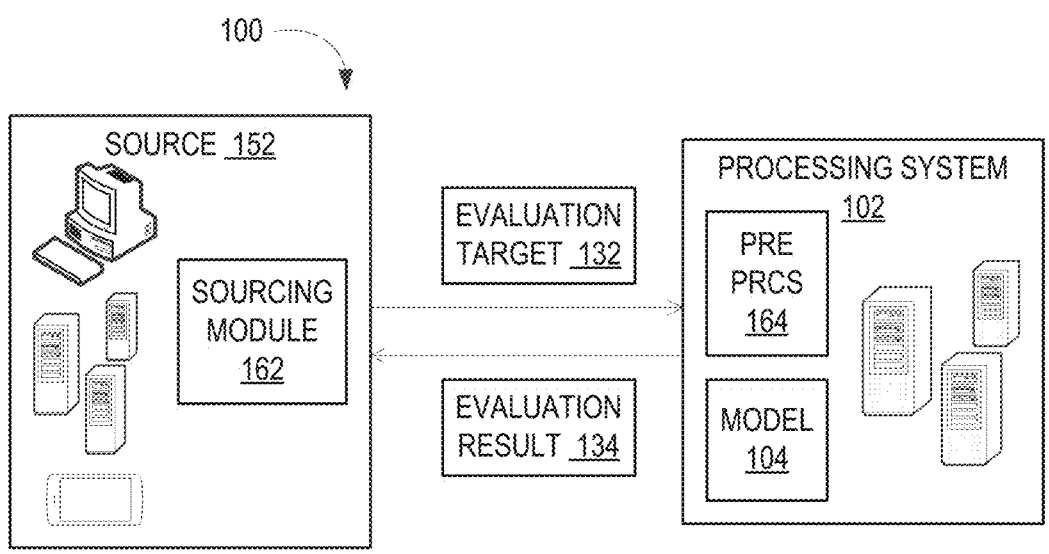

FIGS. 1A and 1B show example operating environments of a computing system 100 including a genetic information processing system 102 (or simply "processing system 102") in accordance with one or more implementations of the present technology. The processing system 102 can include one or more computing devices, such as servers, personal devices, enterprise computing systems, distributed computing systems, cloud computing systems, and/or the like. The processing system 102 can be configured to analyze DNA information diagnosing one or more types of cancer, for evaluating development stages leading up to the onset of the one or more types of cancer, and/or for predicting a likely onset of the one or more types of cancer.

The operating environment depicted in FIG. 1A can represent a development or training environment in which the processing system 102 develops and trains an analysis mechanism, such as an ML model 104, configured to detect a presence, a progress, or a likely onset of one or more types of cancer. In developing and training the ML model 104, the processing system 102 can first identify an analysis template (e.g., specific data locations or values within reference data 112, such as the human genome or other data derived from human/patient DNA) targeted for further analysis and/or consideration.

As an illustrative example, the processing system 102 can use a text-based representation (e.g., one or more text strings) of the human DNA as the reference data 112. The processing data 102 can analyze the reference data 112 to identify specific locations and/or corresponding text sequences that can be utilized as identifiers or comparison points in subsequent processing. In some implementations, the processing system 102 can use a set of unique text segments 113 (e.g., a set of unique TRs) found or expected in the reference data 112 to generate an initial analysis set 114. The processing system 102 can generate the initial analysis set 114 by identifying expected phrases 120 that include the unique segment set 113 and/or by computing derivations thereof (e.g., derived phrases 122) that represent mutations targeted for analysis. The initial analysis set 114 and/or the unique segment set 113 can include location identifiers 118 associated with a relative location of such segments, phrases, and/or derivations within the reference data 112.

The processing system 102 can further use a refinement mechanism 115 (e.g., a software routine or a set of instructions) that further operates on the initial analysis set 114 and/or subsequent data processing. The refinement mechanism 115 can filter results of one or more data processing operations leading up to the designing and/or training of the ML model 104. The refinement mechanism 115 can generate the filtered result of the initial analysis set 114 as the refined set 116. Additionally or alternatively, the refinement mechanism 115 may be configured to filter during or after the feature selection process and/or the sample data 130.

In some implementations, the refinement mechanism 115 can process the unique segment set 113 and/or the initial analysis set 114 to generate a refined set 116. For example, the refinement mechanism 115 can be configured to remove (1) overlapping TRs from the unique segment set 113, (2) remove duplicated phrases from the initial analysis set 114, (3) filter or adjust for the sample data 130 (e.g., text-based DNA data representative of healthy individuals, cancerous tissues, and/or non-cancerous tissues collected from cancer patients) used to develop and/or train the ML model 104, and/or (4) adjust for, or filter, physiological noise or processing noise. Details regarding the derivation of the initial template and refinement thereof are described below.

For the feature selection, the processing system 102 can iteratively add or remove one or more unique locations/sequences and/or derivations from the refined set 116 and calculate a correlation or an effect of the removed datapoint on the known classifications of the sample data 130 (e.g., to accurately recognize the different categories of the sample data 130). The processing system 102 can determine a set of selected features 124 that correspond to the unique locations/sequences and derivations thereof having at least a threshold amount of effect or correlation with one or more corresponding cancer types. In other words, the processing system 102 can determine the set of features 124 including locations, sequences, mutations, or combinations thereof that are deterministic or characteristic of, or commonly occurring in, corresponding cancers. Based on the set of features 124, the processing system 102 can implement an ML mechanism 124 (e.g., a support vector machine (SVM), a random forest, neural network, etc.) to generate the ML model 104. The processing system 102 can further train the ML model 104 using training data.

Using the refined results, the processing system 102 can limit the amount of data considered or processed in subsequent analyses, such as in feature selection, model generation, model training, and/or the like. For example, the processing system 102 can use the refinement mechanism 115 to reduce the size of the unique segment set 113, thereby reducing the expected phrases 120 and the derived phrases 122 that correspond to the unique segment set 113. Also, the processing system 102 can use the refinement mechanism 115 to further reduce the size of the initial analysis set 114, such as by removing potential duplicated phrases (e.g., across expected/derived phrases at different locations). Accordingly, the processing system 102 can reduce the resource consumption through the reduced size of the refined set 116 (e.g., in comparison to the initial analysis set 114) and reduce the noises and other negative impacts generated by the overlapping/duplicative phrases. Additional sample-, process-, or physiology-based refinement can further increase the overall performance and accuracy of the resulting ML model 104.

The operating environment depicted in FIG. 1B can represent a deployment environment in which the processing system 102 applies the analysis mechanism to detect a presence, a progress, and/or a likely onset of one or more types of cancer from an evaluation target 132 (e.g., a text-based form of patient DNA data). The processing system 102 can generate an evaluation result 134 based on testing the evaluation target 132 with the ML model 104. The processing system 102 can generate the evaluation result 134 that represents a cancer diagnosis or a cancer signal. For example, the evaluation result 134 can represent a determination that the patient has cancer, a stage (e.g., clinically recognized stages 1-4) of the onset cancer, a progress state before, or leading up to, an onset of caner, a likelihood of developing cancer within a predetermined period, an identification of the type of cancer, or a combination thereof.

As an illustrative example, the processing system 102 can include a sourcing device 152 that provides the evaluation target 132 and/or receives the evaluation result 134. The sourcing device 152 can be operated by a patient submitting the evaluation target 132, a healthcare service provider associated with the patient, an insurance company, or the like. Some examples of the sourcing device 152 can include a personal device (e.g., a personal computer or a mobile computing device, such as a wearable device, smart phone, or tablet), a workstation, an enterprise device, etc.

In some implementations, the processing system 102 can include a sourcing module 162 that operates on the sourcing device 152. The sourcing module 162 can include a device, circuit, or a software module (e.g., a codec, application program, or the like) that generates or pre-processes the evaluation target 132. For example, the sourcing module 162 can include a homomorphic encoder that encrypts and prevents unauthorized access to the patient data. The evaluation target 132 can include the homomorphically encoded data that can be processed at the processing system 102 without fully decrypting and recovering the patient data. In other words, the processing system 102 can apply the ML model 104 that is configured to process or perform computations on the encrypted data.

The processing system 102 can include a pre-processing module 164 that conditions the evaluation target 132 for and/or during application of the ML model 104. For example, the pre-processing module 164 can include a device, circuit, or a software module (e.g., a codec, application program, or the like) that removes biases or noises introduced before receiving the evaluation target 132 and/or during the processing (e.g., bootstrapping module to remove noise or other uncertainties introduced by processing encrypted data) of the evaluation target 132.

Data Processing Formats

Figure 2:
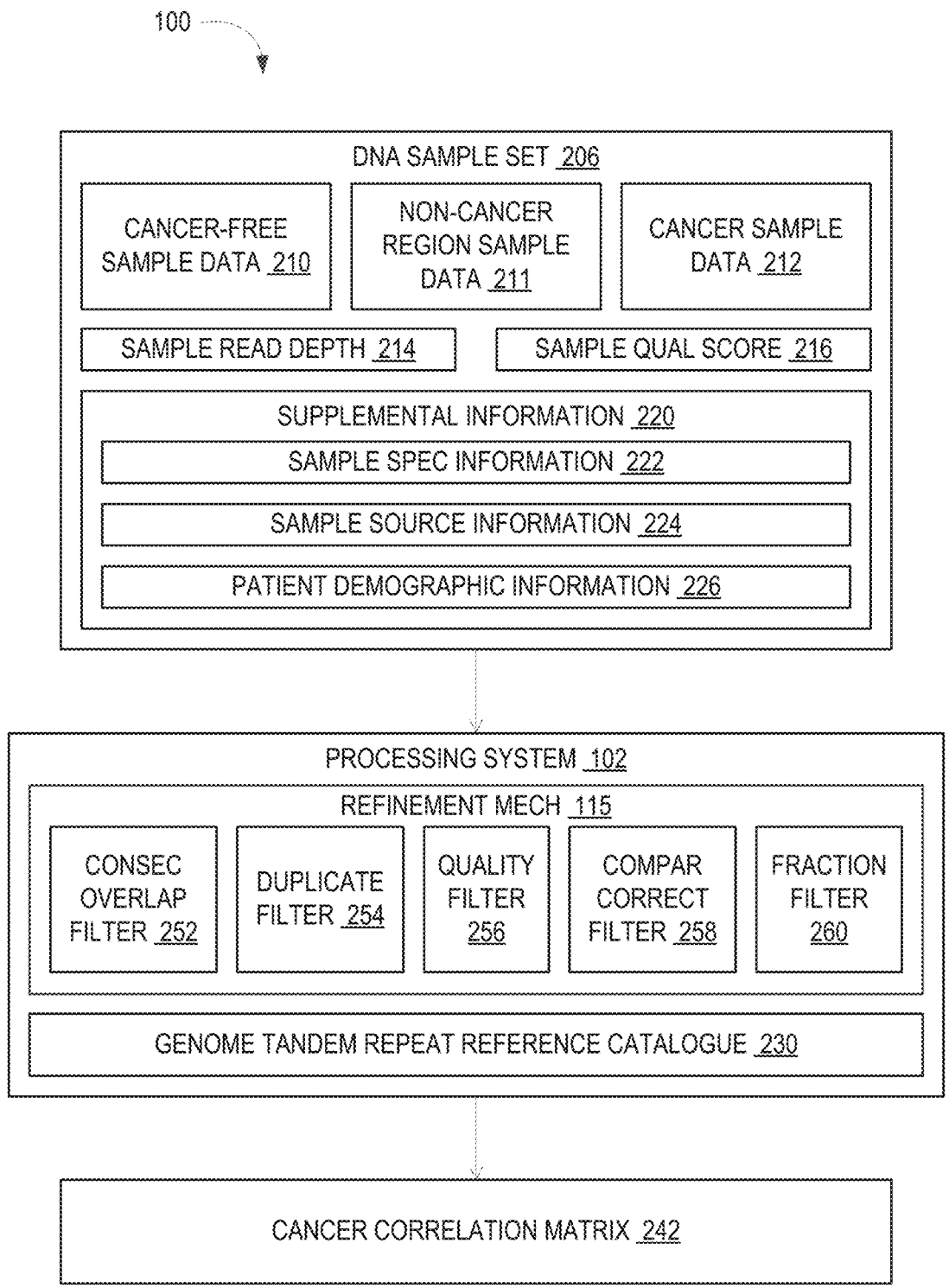
FIG. 2 shows an example data processing format for the genetic information processing system in accordance with one or more implementations of the present technology.

In developing and training the ML model 104 and/or deploying the ML model 104, the processing system 102 can utilize a variety of data processing formats (e.g., data structures, organizations, inputs and outputs, or the like). FIG. 2 shows an example data processing format for the processing system 102 in accordance with one or more implementations of the present technology. The processing system 102 receive and process a DNA sample set 206 (e.g., an instance of the reference data 112 and/or sample data 130 illustrated in FIG. 1A) having one or more of the formats or subfields illustrated in FIG. 2. Moreover, the processing system 102 can generate the initial analysis set 114 (FIG. 1A) and the refined set 116 (FIG. 1A) using one or more detailed example aspects illustrated in FIG. 2.

As an illustrative example, the DNA sample set 206 can include DNA data (e.g., representative of a set of sequenced DNA information) corresponding to different known categories. Examples of the DNA sample set 206 can include genetic information (e.g., text-based representations) derived or extracted from human bodies, such as from tissue extracted during a biopsy or from cell-free DNA (e.g., DNA that is not encapsulated within a cell) in bodily fluids. The DNA sample set 206 can include DNA data collected from volunteers or participating patients having medically confirmed diagnoses and/or from public or private databases.

The DNA sample set 206 can include data collected from different types and/or categories of samples, such as cancer-free samples (cancer-free sample data 210), samples taken from non-cancerous regions (non-cancer region sample data 211), and/or cancerous samples (cancer sample data 212). The cancer-free sample data 210 (or simply "cancer-free data") can represent text-based DNA data corresponding to samples collected from patients confirmed/diagnosed to be cancer free. The non-cancer region sample data 211 (also called "non-regional data") can represent text-based DNA data corresponding to samples collected from non-cancerous regions (e.g., white blood cells or leukocytes) of patients confirmed/diagnosed to have one or more types of cancer. The cancer sample data 212 (also called "cancer-specific data") can represent text-based DNA data corresponding to samples (e.g., tumor biopsies, liquid biopsies, etc.) collected from cancerous regions or tumors confirmed/diagnosed to be a specified type of cancer. The DNA sample set 206 can include information (e.g., the non-regional data 211 and/or the cancer-specific data 212) corresponding to one or more types of cancers (e.g., breast cancer, lung cancer, colon cancer, and/or the like).

The DNA sample set 206 can further include descriptions regarding a strength or a trustworthiness of the data. For example, the DNA sample set 206 can include a sample read depth 214 and/or a sample quality score 216. The sample read depth 214 can represent a number of times that a given nucleotide in the genome (e.g., certain text string/portion) was detected in a sample. The sample read depth 214 may correspond to a sequencing depth associated with processing fragmented sections of the genome within a tissue sample. The sample quality score 216 can represent a quality of identification of the nucleobases generated by DNA sequencing. In some implementations, the sample quality score 216 can include a Phred quality score.

The DNA sample set 206 can also include supplemental information 220 that describes other aspects of the sample or the source of the data. For example, the supplemental information 220 can include information such as sample specification information 222 (or simply "specification information"), sample source information 224 (or simply "source information"), patient demographic information 226, or a combination thereof.

The specification information 222 can include technical information or specifications about the sequenced DNA associated with the DNA sample set 206. For example, the specification information 222 can include information about the locations 118 (FIG. 1A) within the genome to which the DNA fragments correspond, such as intron and exon regions, specific genes, or chromosomes. Also, the specification information 222 can describe, for example, (1) the process, methods, and instrumentation used to extract and sequence the genetic material, (2) the number of sequencing reads for each sample, or a combination thereof.

The source information 224 can include details regarding the source and/or the categorization of the sample. For example, the source information 224 can include information about the cancer type, the stage of cancer development, the organ or tissue from which the sample was extracted, or a combination thereof.

The patient demographic information 226 can include demographic details about the patient from which the sample was taken. For example, the patient demographic information 226 can include the age, the gender, the ethnicity, the geographic location of where the patient resides/visited, the duration of residence/visitation, predispositions for genetic disorders or cancer development, family history, or a combination thereof.

The processing system 102 can analyze the DNA sample set 206 using the mutation analysis mechanism. Accordingly, the processing system 102 can identify mutations or mutation patterns in specific DNA sequences that can be used as markers to determine the existence, the progress, and/or the developing stages of a particular form of cancer. To identify the relevant mutations, the processing system 102 can detect a set of targeted locations or text patterns (e.g., according to the TRs) within the reference genomes.

The processing system 102 can generate and/or utilize a genome tandem repeat reference catalogue 230 that represents a catalogue or a collection of uniquely identifiable TRs in the human genome. As an example, the genome tandem repeat reference catalogue 230 can be based on a reference human genome (e.g., the reference data 112), such as the GRCh38 reference genome. The uniquely identifiable TRs can include DNA sequences having therein a series of multiple instances of directly adjacent identical repeating nucleotide units or base patterns, such as microsatellite DNA sequences. The base patterns can have a predetermined length, such as one for a repetition of one letter or monomer (e.g., 'AAAA') or greater (e.g., three for tetramers, such as 'ACT'). Such uniquely identifiable TRs can serve as reference sequences (e.g., reference locations within the human genome) or markers for evaluating the DNA sample set 206. Since the DNA sample set 206 may correspond to incomplete DNA fragments, the unique TRs found within the fragments may be used to map the DNA information to the human genome.

The processing system 102 can use the genome tandem repeat reference catalogue 230 to compute the initial analysis set 114. For example, the processing system 102 can use the unique TRs identified in the genome tandem repeat reference catalogue 230 to generate derived strings that represent potential mutations. In some implementations, the processing system 102 can identify text characters preceding and/or following each unique TR and derive the mutation strings that represent one or more types of mutations (e.g., insertion-deletion mutations—also called "indel mutations" or "indels"). Details regarding the initial analysis set 114 (e.g., strings with flanking characters and/or mutation strings) are described below.

The processing system 102 can compare the mutations at the targeted locations/sequences across the different types of DNA sample set 206. Based on the comparison, the processing system 102 can compute a correlation between, or a likely contribution of, the mutations at the targeted locations/sequences and the development of cancer. Accordingly, the processing system 102 may generate a cancer correlation matrix 242 that correlates identified tumorous sequences or text-based patterns to specific types of cancer. For example, the cancer correlation matrix 242 can be an index that includes multiple instances of the uniquely identifiable TRs in the genome TR reference catalogue 230 that, when found to be tumorous, indicate the existence of a particular form of cancer or indicate the possibility that a particular form of cancer will develop.

The processing system 102 can perform the feature selection using the cancer correlation matrix 242, such as by retaining the locations/sequences and/or derived mutation patterns having at least a predetermined degree of correlation to one or more corresponding types of cancer. Using the selected features, the processing system 102 can develop and train the ML model 104 configured to detect, predict, and/or evaluate development or onset of cancer.

In some implementations, the processing system 102 can further use the refinement mechanism 115 to generate the refined set 116 (FIG. 1A). The refinement mechanism 115 may include one or more filters to enhance the genome TR reference catalogue 230, the initial analysis set 114, and/or corresponding features, such as by removing or adjusting one or more erroneous or unnecessary sequences. For example, the refinement mechanism 115 can include: (1) a consecutive overlap filter 252 configured to remove consecutive or overlapping sequences (e.g., unique TRs) that effectively point to the same location, (2) a duplicate filter 254 configured to remove duplicate sequences, such as between mutation strings at different locations, (3) a quality filter 256 configured to remove/adjust for input sample data, such as based on quality and/or input depth, (4) a comparison correction filter 258 configured to remove computational noise or errors, (5) a physiology-based filter, such as a fraction filter 260, configured to remove or adjust for physiological features and/or collection-based features that interfere with the data processing, or a combination thereof. Details regarding the refinement mechanism 115 is described below.

Base Text Patterns—Segments

Figures 3A, 3B:
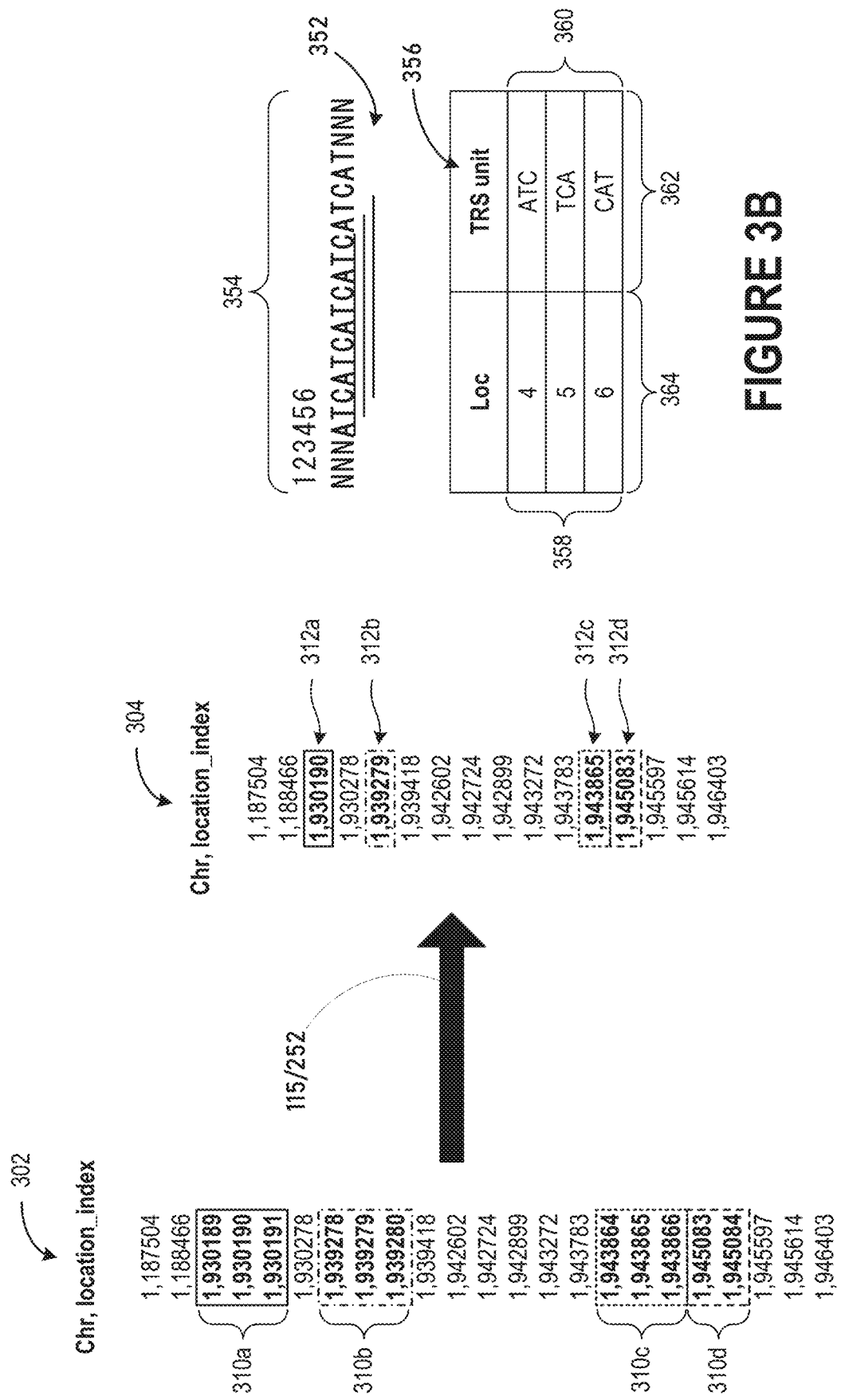
FIGS. 3A and 3B (SEQ ID NO: 19) show examples of unique segments and refinements thereof in accordance with one or more implementations of the present technology.

For describing further detailed aspects of the data format, FIGS. 3A and 3B show examples of unique segments (e.g., uniquely identifiable TRs within the human genome) and refinements thereof in accordance with one or more implementations of the present technology. FIG. 3A shows an initial segment set 302 and a refined segment set 304 that correspond to the unique segments 113 of FIG. 1. FIG. 3B illustrates example overlaps 352 in the initial segment set 302. Referring to FIGS. 3A and 3B together, the processing system 102 can use the refinement mechanism 115 (e.g., the consecutive overlap filter 252) to remove the overlaps 352 therein and generate the refined segment set 304.

In some implementations, the processing system 102 can generate the initial segment set 302 based on analyzing the reference data 112 (FIG. 1A) to find uniquely identifiable patterns. For example, the processing system 102 can generate the initial segment set 302 by identifying uniquely identifiable TRs within the human genome. The processing system 102 can use base or TR units (e.g., base character patterns having controllable lengths of one or more characters that are repeated) to identify the overall TR or segment having a corresponding length (e.g., two or more multiples of the TR unit length). The processing system 102 can generate the initial segment set 302 by including repeated patterns of the TRs that exceed a minimum number of base pairs. For example, the repeated TR sequence can be selected based on using the repeated base unit having the minimum number of base pairs ranging between five and eight base pairs.

In the initial segment set 302, the processing system 102 may end up including the overlaps 352 that effectively correspond to a longer and unique string segment and the corresponding location. For the example illustrated in FIG. 3B, a target sequence 354 (e.g., a sequence/combination of nucleotides, such as a portion of the DNA information) can include a uniquely identifiable segment ('ATCATCATCATCATCAT' (SEQ ID NO: 9) having 17 characters). The processing system 102 can identify unique segments 360 within the target sequence 354 based on identifying repeated adjacent patterns of base units 362. The length of the repeated base units 362 and/or the number of repeats may be predetermined or adjusted in generating the initial segment set 302. For the illustrated example, the targeted segment length corresponds to 12 characters or four repeats of three-letter TR units. Along with the repeated base units 362, the unique segments 360 can be identified based on corresponding segment locations 364 that identify positions (e.g., first letter positions) of the segments within the target sequence 354.

When the target sequence 354 includes a repeated pattern that exceeds the targeted segment length, one target sequence 354 can be identified as including repeats of multiple instances of the base units 356 (e.g., 'ATC,' 'TCA,' and 'CAT'). The multiple instances of the base units 356 may correspond to shifted results of each other. As such, the multiple unique segments 360 can overlap each other and/or be sequentially shifted by one or more characters relative to each other. FIG. 3A illustrates a portion of the initial segment set 302 having overlapping location sets 310a, 310b, 310c, and 310d that correspond to such overlapping instances of the unique segments 360. However, given the nature of the overlaps, each of the overlapping location sets 310a, 310b, 310c, and 310d can effectively correspond to a single segment/location rather than the multiple separate segments/locations.

The processing system 102 can use the refinement mechanism 115 to identify and remove the overlaps 352 in the unique segments 360. In some implementations, the consecutive overlap filter 252 can be configured to ensure that the initial segment set 302 is sorted according to the segment location 358. With the sorted segments, the consecutive overlap filter 252 can identify patterns in the segment location 358 of adjacent segments within the initial segment set 302. The consecutive overlap filter 252 can be configured to identify the overlaps 352 when the segment location 358 of the adjacent segments are separated by a predetermined number (e.g., one, two, or more, a number based on the repeated unit length and/or the targeted segment length, and/or the like). Also, the consecutive overlap filter 252 can be configured to identify the overlaps 352 when the segment location 358 follows one or more pattern (e.g., consistently separated by one or two values) over two, three, or more adjacently occurring segments. The consecutive overlap filter 252 can group the two or more adjacent segments that satisfy the separation threshold/pattern as a set of the overlaps.

Additionally or alternatively, the consecutive overlap filter 252 can configured to identify the overlaps 352 when the repeated base units 356 for the adjacent segments correspond to circularly shifted values. For the example illustrated in FIG. 3B, the processing system 102 can identify that the unique segments 360 at locations 4, 5, and 6 correspond to an overlapping set since the repeated base units 356 of 'ATC,' 'TCA,' and 'CAT' correspond to circularly shifting a preceding unit by one character/position. The consecutive overlap filter 252 can group the two or more adjacent segments that satisfy/maintain the detected pattern in the repeated base units 356 a set of the overlaps.

After the sets of overlaps are identified, the consecutive overlap filter 252 can refine the set by reducing the number of overlapped segments. For example, the consecutive overlap filter 252 can retain one segment from each set of overlaps and remove others. In some implementations, the consecutive overlap filter 252 can be configured to select the segment according to a predetermined location, the target segment length, the repeated unit length, or a combination thereof. For example, the consecutive overlap filter 252 can be configured to select the segment positioned in the middle/center of the set. Also, the consecutive overlap filter 252 can include a predetermined equation that identifies the selection location according to the number of segments in the set, the target segment length, the repeated unit length, or a combination thereof. The selected locations can be represented as refined locations (e.g., refined locations 312a, 312b, 312c, and 312d respectively corresponding to overlapping sets 310a, 310b, 310c, and 312d) in the refined segment set 304.

Base Text Patterns—Expected Phrases

Figure 4:
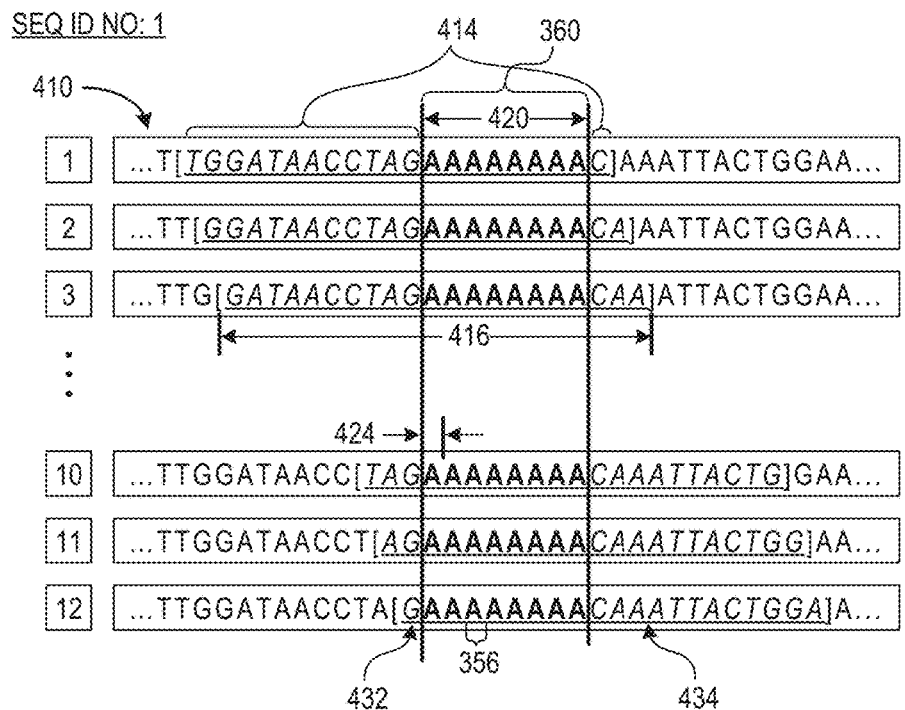
FIG. 4 shows example expected phrases in accordance with one or more implementations of the present technology.

The processing system 102 can use the processed segments (e.g., the refined segment set 304) to generate phrases. FIG. 4 shows example expected phrases 410 in accordance with one or more implementations of the present technology. The expected phrases 410 can correspond to textual representations of the DNA sequences or a set of sequence variations that may be used as bases for subsequent processing/comparing, such as in deriving mutations strings and analyzing the DNA sample set 206 (FIG. 2).

For context, samples collected from patients may include fragments or portions of the overall DNA. As such, the corresponding sequenced values or the text string may include different combinations of characters. The processing system 102 (FIG. 1A) can generate the expected phrases 410 as representations of different character combinations that include the uniquely identifiable segments (e.g., the refined segment set 304 (FIG. 3A), such as the refined set of unique TRs).

Accordingly, the processing system 102 can generate the expected phrases 410 based on the refined segment set 304 instead of the initial segment set 302 (FIG. 3A). In some implementations, the processing system 102 can generate a set (illustrated as a unique sequence identifier number in FIG. 4) of the expected phrases 410 for each of the unique segments 360 (illustrated using bolded characters in FIG. 4) in the refined segment set 304.

The expected phrases 410 can have a phrase length 416 of k (e.g., generally between 10 to 50, but could be greater than 50 or fewer than 10) number of DNA base pairs or pairs of nucleobases. Each DNA base pair can be represented as a single text character (e.g., 'A' for adenine, 'C' for cytosine, 'G' for guanine, and 'T' for thymine). As such, the expected phrases 410 may also be referred to as "k-mers."

In some implementations, as described above, the unique segments 360 can include a DNA sequence of a specified minimum length. A unique segment 360 can include a series of multiple instances of directly adjacent identical repeating nucleotide units or the repeated base units 356. For example, the unique segment 360 can include a minisatellite DNA or microsatellite DNA sequence of a specified minimum length. Accordingly, the unique segment 360 can correspond to a repeated pattern of the repeated base units 356, and the number of repetitions can correspond to a segment length 420 (e.g., the total length of, or total number of, nucleotide base pairs) for the unique segment 360. The repeated base unit 356 can have a base unit length 424 corresponding to the number of nucleotides within the repeated base unit 356 (e.g., one for a mono-nucleotide, two for a di-nucleotide, etc.).

For illustrative purposes, FIG. 4 shows a specific instance for the unique segment 360 of "AAAAAAAA," annotated as "A8," located at the molecular position starting at "10, 513,372" on chromosome 22. In this example, the unique segment 360 includes the segment length 420 of eight base pairs with the repeated base unit 356 of one base pair (e.g., a monomer or a mono-nucleotide) 'A.'

The processing system 102 can use the phrase length 416 (e.g., k between 10 to 50 base pairs) that has been predetermined or selected to capture targeted amount of data/characters surrounding the unique segments 360. As such, the phrase length 416 can be greater than the segment length 420, and each of the expected phrases 410 can include a set of flanking texts 414 (e.g., text-based patterns; illustrated using italics in FIG. 4) preceding and/or following the corresponding unique segment 360.

The processing system 102 can generate the expected phrases 410 in a variety of ways. As an illustrative example, the processing system 102 can use each of the unique segments 360 as an anchor for a sliding window having a length matching the phrase length 416. The processing system 102 can iteratively move the sliding window relative to the unique segment 360 and log the text captured within the window as an instance of the expected phrases 410. As such, each of the expected phrases 410 can correspond to a unique position of the sliding window relative to the unique segment 360. Also, the set of expected phrases 410 for one reference TR can include different combinations of the flanking text 414 (e.g., a combination of one or more leading characters 432 and/or one or more tailing characters 434).

The total number of base pairs in flanking text 414 can be a fixed value that is based on the phrase length 416 and the segment length 420. The number of characters in the flanking text 414 can be calculated as the difference between the phrase length 416 and the segment length 420. As an example, for one of phrases having a length of 21 base pairs and a segment length of 8 base pairs, the flanking text can include 13 base pairs.

Each of the expected phrases 410 can represent one of a number of position variant k-mers based on the flanking texts 414. The position variant k-mers can include specific numbers of base pairs in the leading flanking text 432 and tailing flanking text 434. For example, a set of the expected phrases 410 can include the same unique segment (e.g., repeated pattern of the TR) and differ from one another according to the number of base pairs included in the leading flanking text 432 and/or the tailing flanking text 434. In general, the number of base pairs included in the leading flanking text 432 and tailing flanking text 434 can vary inversely between the different instances of the position variant k-mers or expected phrases 410.

As an example, each of the expected phrases 410 illustrated in FIG. 4 has the phrase length 416 of 21 base pairs and the segment length 420 of 8 base pairs. A first expected phrase can have the leading characters 432 corresponding to 12 base pairs and the tailing character 434 corresponding to 1 base pair. A second expected phrase can have the leading characters 432 corresponding to 11 base pairs and the tailing characters 434 of 2 base pairs. The pattern can be repeated until the last expected phrase has the leading characters 432 corresponding to 1 base pair and the tailing characters 434 corresponding to 12 base pairs.

The expected phrases 410 can be grouped into sets that each correspond to a unique segment as described above. The total number of phrases or position variant k-mers (position variant total) in the grouped set can be represented as:

Position Variant Total=(Phrase length $k$)−(Segment length)−1.

For the example illustrated in FIG. 4, the set of expected phrases can have a position variant total of 12, representing 12 different instances of phrases corresponding to the phrase length 416 of 21 and the segment length 420 of 8.

In some implementations, the processing system 102 can use the unique instances of the TRs as the basis for generating the sets of expected phrases 410. Accordingly, each of the expected phrases 410 can also be unique since it is generated using the corresponding unique TR as a basis. The processing system 102 can use the unique expected phrases 410 to account for and identify the fragmentations likely to be included in the patient samples.

Base Text Patterns—Derived Phrases

The processing system 102 can use the expected phrases 410 to analyzes mutations in genetic information (e.g., sequenced DNA segments), such as for detecting tumorous/cancerous DNA sequences. The expected phrases 410 can be used to detect locations within the reference genome and related mutations that are indicative of certain types of cancers or likely onset thereof. The processing system 102 can use the expected phrases 410 as basis to generate derived phrases that represent various mutations in the genetic information. The processing system 102 can use the derived phrases to recognize or detect mutations in the DNA sample set 206 (FIG. 2), the sample data 130 (FIG. 1A), or the like in developing, training, and/or deploying the ML model 104. Effectively, the processing system 102 can identify the mutation patterns indicative of certain types of cancers based on using the derived phrases to determine differences between healthy and cancerous DNA samples (e.g., between the cancer-free data 210, the non-regional data 211, and/or the cancer-specific data 212 illustrated in FIG. 2).

Figure 5:
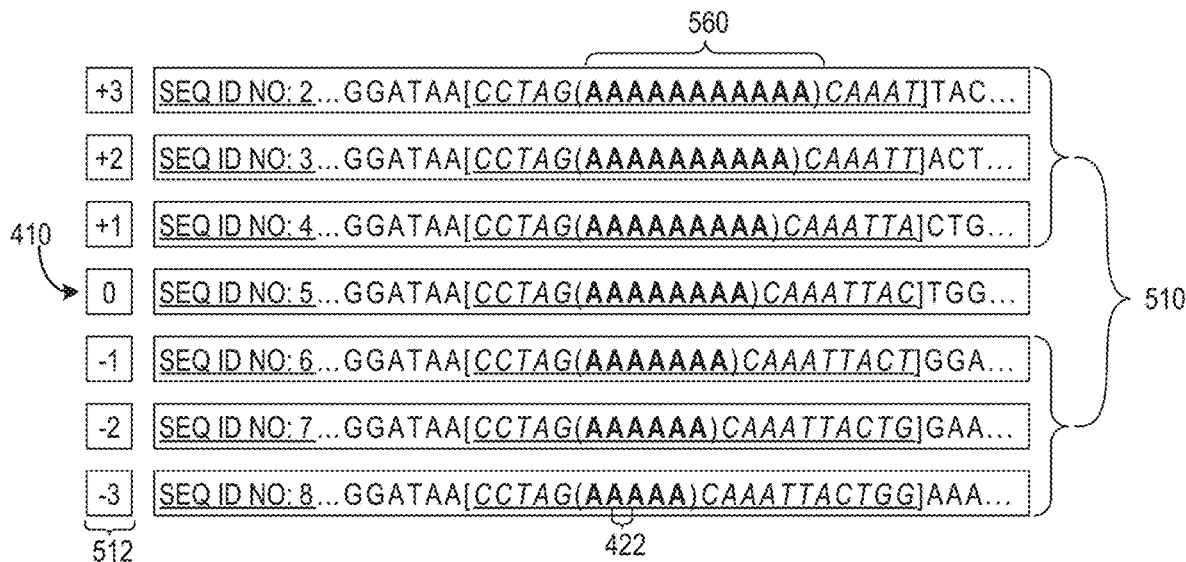
FIG. 5 shows example derived phrases in accordance with one or more implementations of the present technology.

FIG. 5 shows example derived phrases 510 in accordance with one or more implementations of the present technology. The processing system 102 (FIG. 1A) can generate the derived phrases 510 based on adjusting the expected phrases 410 expected to a predetermined pattern. For example, for one or more or each of the expected phrases 410, the processing system 102 can generate a set of the derived phrases 510 that represent indel mutations of the corresponding expected phrase 410. In some implementations, the processing system 102 can generate the set of derived phrases 510 that correspond to a predetermined number of insertions and/or deletions in the unique segment 360 (FIG. 4) within the corresponding expected phrase 410. In other words, the set of derived phrases 510 can represent the indel variants of the sequence represented by the corresponding expected phrase 410.

The processing system 102 can generate the set of the derived phrases 510 based on adjusting (via insertion/deletion) the number of the repeated base units 356 (FIG. 4) and/or one or more characters in the unique segment 360 of the expected phrase 410. Accordingly, the processing system 102 can generate a set of derived segments 560 that correspond to indel variants of the unique segment 360.

The processing system 102 can generate the derived phrases 510 based on adding and/or adjusting the flanking text 414 (FIG. 4) around the derived segments 560 (illustrated as the bolded characters within parentheses '( )'). In some implementations, the processing system 102 can generate the derived phrases 510 having the same phrase length 416 (FIG. 4) as the expected phrases 410. As a result, the processing system 102 can expand or reduce the coverage of the flanking text 414 according to the indel changes to the unique segment 360 (e.g., the originating pattern of TRs). With deletions, the processing system 102 can include corresponding number of new characters from the overall sequence into the flanking text 414 (FIG. 4). Similarly with additions, the processing system 102 can remove the corresponding number of characters from the flanking text 414. For illustrative purposes, FIG. 5 shows the surrounding adjustments occurring in the trailing characters 434 (FIG. 4) while maintaining the leading characters 432 (FIG. 4). However, it is understood that the processing system 102 can operate differently, such as by (1) adjusting the leading characters 432 while maintaining the trailing characters 434 and/or (2) spreading the adjustments across the leading characters 432 and the trailing characters 434 according to the number of characters in the original phrase and/or a predetermined pattern.

For the example illustrated in FIG. 5, the expected phrase 410 can correspond to the repeated TR sequence of "AAAAAAAA" or A8 beginning at position 10,513,372 on chromosome 22. The derived phrases 510 can correspond to the derived segments 560 including up to three insertions and deletions of the repeated base unit 'A.' In other words, the derived phrases 510 can correspond to phrases built around A5, A6, A7, A9, A10, and A11.

The number of the derived phrases 510 associated with a given expected phrase can be determined by an indel variant value 512. The indel variant value 512 can include an integer value representative of the number of insertions and deletions. The indel variant value 512 can further function as an identifier for a phrase. For example, the indel variant value '0' can represent the expected phrase 410 having zero insertions/deletions. Positive indel variant values (e.g., 1, 2, 3) can represent derived phrases including corresponding number of insertions of base units or characters in the repeated TR portion. Negative indel variant values (e.g., −1, −2, −3) can represent derived phrases corresponding number of deletions of base units or characters in the repeated TR portion. For the example illustrated in FIG. 5, the indel variant values 1, 2, and 3 can represent/identify A9, A10, and A11, respectively. Also, the indel variant values −1, −2, and −3 can represent A7, A6, and A5, respectively.

For context, the processing system 102 can use the expected phrases 410 and the corresponding sets of derived phrases 510 to analyze the DNA sample set 206 and develop/test the ML model 104 (FIG. 1A). The phrases generated using the unique TR patterns can provide accurate and precise identification of corresponding sequences in the different types of health and cancerous DNA samples. In other words, the various phrases can represent the type of textual patterns or the corresponding sequences that are targeted for analyses and comparisons between the cancer-free data 210, the non-regional data 211, and/or the cancer-specific data 212. For example, the processing system 102 can use the various phrases to identify the numbers and types/locations of mutations in the cancer-related samples and absent in healthy samples. The processing system 102 can aggregate the results across multiple samples and patients to derive a pattern or a correlation between certain types of mutations and the onset of certain types of cancer.

To put things another way, the processing system 102 can identify unique patterns (e.g., the unique TR patterns and/or the corresponding expected phrases 410) that each occur once within the human genome. The unique patterns can be used to identify specific locations and portions within the human genome for various analyses. Moreover, the processing system 102 can target specific types of mutations, such as indel mutations, in developing a cancer-screening tool and/or a cancer-predicting tool. It has been found that various types of cancers can be accurately detected and progress/status of such types of cancers can be described using the expected phrases 410 and the corresponding sets of the derived phrases 510 (e.g., sequences identified using unique TR-based patterns and indel variants thereof) and without considering other aspects/mutations of the human DNA. As a result, the processing system 102 can generate the ML model 104 that can accurately detect the existence, predict a likely onset, and/or describe a progress of certain types of cancers using the various phrases. In other words, the processing system 102 can detect/predict the onset of cancer without processing the entire DNA sequence and different types of mutation patterns.

The processing system 102 can further improve the efficiency and reduce the resource consumption using the indel variant value 512. Given the downstream processing methodology, the indel variant value 512 can control the number of phrases considered in developing/training the ML model 104 and thereby affect the overall number of computations and the amount of resource consumption. When the indel variant value 512 is too high, the processing system 102 may end up analyzing a reduced or ineffective number of possible sequences. For example, as the total number of base pairs in the TR indel variant approaches the phrase length 416, the number of available derived phrases and the likely occurrence of such mutations decrease. Accordingly, in some implementations, the indel variant value 512 in the range of three to five provides sufficient coverage for varying degrees of possible insertion and deletion mutations that are indicative of one or more types of cancer. This range of values may be sufficient to provide accurate results without requiring ineffective or inefficient amount of computing resources.

Additionally, the processing system 102 can further improve the efficiency and reduce the resource consumption using the segment length 420 (e.g., the length of the uniquely identifiable TR-based pattern). It has been found that the probability of mutation occurrences decreases as the tandem repeat segment length 420 is reduced. In particular, the mutation rate for genome TR sequences with segment length 420 of fewer than five base pairs is significantly less than genome TR sequences with segment length 420 of five or more base pairs. Thus, the expected phrases 410 can be selected as the genome TR sequence with segment length 420 of five or greater.

Figure 6:
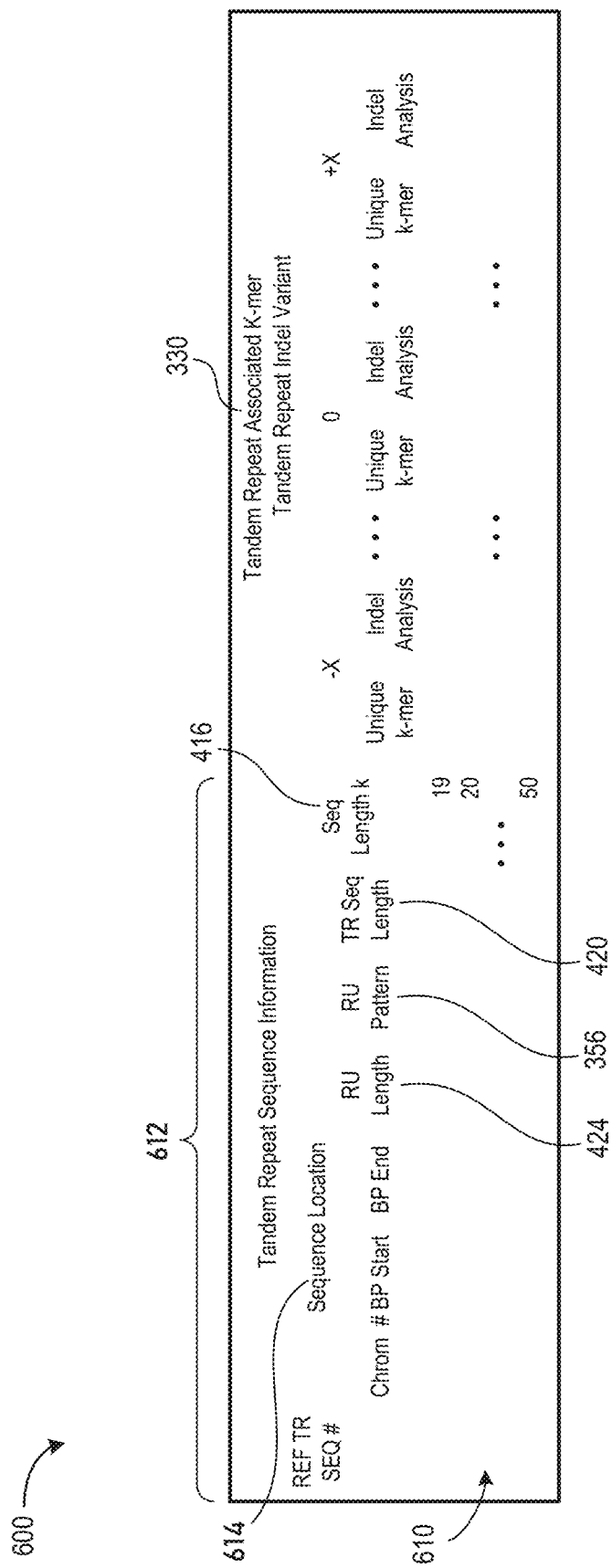
FIG. 6 shows an example analysis template in accordance with one or more implementations of the present technology.

The processing system 102 can store the various phrases (e.g., the expected phrases 410 and/or the corresponding sets of the derived phrases 510) in the genome TR reference catalogue 230 (FIG. 2). FIG. 6 shows an example analysis template 600 in accordance with one or more implementations of the present technology. The processing system 102 can use the analysis template 600 to represent the various phrases and/or track the associated processing results.

In some embodiments, the analysis template 600 can correspond to a format for the genome TR reference catalogue 230. The genome TR reference catalogue 230 can include catalogue entries 610 for each instance of the unique segments 360 (e.g., uniquely identifiable TR patterns or reference TR patterns). The entries 610 can include TR sequence information 612 that characterizes the unique segments 360 and/or the derived segments 560. For example, the TR sequence information 612 can include a sequence location 614, the segment length 420, the base unit length 424, the repeated base unit 356, or a combination thereof.

The sequence location 614 can identify the location of the corresponding unique segment 360 and/or expected phrase 410 within the reference genome. As an example, the sequence location 614 can be described based on the molecular location of the unique segment 360, such as (1) the chromosome on which the TR sequence is located and/or (2) the base pair numbers in the chromosome marking the beginning/ending of the TR sequence. The sequence location 614 can act as a unique identifier that distinguishes one instance of the unique segment 360 and/or the expected phrase 410 from another. For example, expected phrases 410 that share the same repeated base unit 356 and the base unit length 424 can be distinguished from one another based on the sequence location 614.

The entries 610 for each instance of the unique segment 360 can include information for one or more instances of the corresponding phrases (e.g., expected and/or derived). For example, the entries 610 can include information for the expected phrases 410 and/or the derived phrases 510 with various values for the phrase length 416. For illustrative purposes, this instance of entries 610 is shown including information for the expected phrases 410 with phrase lengths corresponding from 19 base pairs to 60 base pairs. However, it is understood that the entries 610 can include information regarding expected phrases 410 with fewer than 19 base pairs and/or greater than 60 base pairs. As another example, the entries 610 can include information that distinguishes between the expected phrases 410 and the derived phrases 510. In some implementations, the entries 610 can identify expected phrases 410 associated with a corresponding TR pattern. For instance, the TR pattern of 'A8' beginning at position 10,513,372 can yield 16 sequences or expected phrases 410 having the phrase length 416 of 30 base pairs.

The entries 610 can further identify the derived phrases 510 that are absent from the reference genome. For illustrative purposes, Table 1 below summarizes the derived phrases 510 having the segment length 416 of 30 base pairs for the unique segment 360 or TR pattern of 'A8' beginning at position 10,513,372 (annotated as '372) on chromosome 22. In this example, each of the derived phrases 510 corresponding to indel variants with the indel variant value 512 ranging from "−5" to "+5" are not found in the reference genome.

TABLE 1

Chromosome 22, '372, "A8" Reference TR Associated Indel Phrase Summary

| Indel Variant Value | Position Variant Total | Total That Do Not Appear |
|---|---|---|
| +5 | 16 | 16 |
| +4 | 17 | 17 |
| +3 | 18 | 18 |
| +2 | 19 | 19 |
| +1 | 20 | 20 |
| −1 | 22 | 22 |
| −2 | 23 | 23 |
| −3 | 24 | 24 |
| −4 | 25 | 25 |
| −5 | 26 | 26 |

The analysis template 600 can be used to track the statistical data generated during development/training of the ML model 104. For example, the processing system 102 can track the occurrences of certain mutations according to the sequence location 614 or the identifier for the corresponding entry 610 and the indel mutation offset/identifier. The processing system 102 can use the counted occurrences for each sample, each sample set, or a combination thereof to compute the correlation between the mutations and the onset of the corresponding type of cancer.

In some implementations, the processing system 102 can calculate the number of occurrences for each of the expected and/or derived phrases, such as for indel variants with or without indel variant '0,' in the patient sequencing data. For each set of phrases associated with a particular indel variant type, the processing system 102 can calculate a statistical value (e.g., a median value) from the set of the number of occurrences. The median value can represent the counts associated with the particular TRS with a particular type of indel variant in the corresponding patient.

As an illustrative example, the processing system 102 can process three TR sequences derived from a targeted k=16 wild-type nucleotide (e.g., ATCATCATC) as shown below in Table 2.

TABLE 2

| TR Sequence Associate K-mers (Underlined) | SEQ ID NO | K-mer Count |
|---|---|---|
| ...ACTTGAATCATCATCATCCTCCTA... | 10 | 7 |
| ...ACTTGAATCATCATCATCCTCCTA... | 11 | 11 |
| ...ACTTGAATCATCATCATCCTCCTA... | 12 | 10 |

The processing system 102 can calculate the median value of the counts as 10. Accordingly, the processing system 102 can assign a count of 10 to a corresponding TR sequence indel type (e.g., indel type +1) for this patient.

The analysis template 600 is shown for exemplary purposes as a template with a general layout for organizing information for each of the segments and/or phrases. It is understood that the analysis template 600 can include different categorizations and arrangements with additional or different pieces of information. Further, it is understood that an active or "in use" version of the genome TR reference catalogue 230 can be populated with values corresponding to the various categories of the entries 610.

In addition to carefully selecting the processing parameters (e.g., the indel variant value 512 and/or the segment length 420) and reducing the overlaps 352 in the unique segments 360 described above, the processing system 102 can further increase the processing efficiencies and accuracy of the ML model 104 by removing duplicate phrases or k-mers. The processing system 102 can inadvertently introduce or generate the duplicate phrases since the derived phrases 510 are generated by altering the unique segments 360. In other words, the derived phrases 510 may include character sequences that match other phrases corresponding to other portions of the human genome (e.g., derived and/or unique phrases corresponding to different locations or TR combinations). The processing system 102 can use the refinement mechanism 115 (e.g., the duplicate filter 254 (FIG. 2)) to identify and remove such duplicated phrases.

In some implementations, the duplicate filter 254 can be configured to compare the derived phrases 510 to the expected phrases 410 corresponding to different locations in the human genome. Additionally or alternatively, the duplicate filter 254 can be configured to compare the derived segments 560 to the unique segments 360 associated with other locations. Moreover, the duplicate filter 254 can compare the derived phrases 510 and/or derived segments 560 across different locations to find matches. For example, the processing system 102 can sort the phrases according to the unique segments 360 and/or the repeated base unit 356 and then according to the base unit length 424. The duplicate filter 254 can be configured to remove one or more or all of the instances of the matching phrases (having, e.g., same base TR units and TR-pattern length). In other words, the duplicate filter 254 can remove from further processing character combinations representative of sequences/mutations that can be found at multiple locations in the human genome. Accordingly, the processing system 102 can ignore the potentially misleading character patterns in analyzing for correlations to different types of cancers and reduce the overall number of processed phrases.

Downstream Filtering

In addition to the text-based filtering described above, the processing system 102 can further filter the data and/or the processing results. For example, the processing system 102 can use the quality filter 256 (FIG. 2) to preprocess and/or adjust for the input patient data, such as the DNA sample set 206. The processing system 102 can use the quality filter 256 to reduce, remove, or adjust for imperfections (e.g., biases caused by inaccurate/insufficient reads) that may be introduced by sequencing technologies. In some implementations, the quality filter 256 can adjust for or normalize different read depths (e.g., the number of times that a given nucleotide in the genome was detected in a sample) across the separately sequence data, such as across the cancer-free data 210, the non-regional data 211, and/or the cancer-specific data 212.

To adjust for the different read depths, the quality filter 256 can be configured to require minimum read depths for the input patient data. In other words, the quality filter 256 can remove or filter out samples and/or corresponding sequenced strings having the sample read depth 214 (FIG. 2) less than a predetermined threshold (e.g., 10). Additionally or alternatively, the quality filter 256 can be configured to normalize the read depths to a predetermined depth (e.g., 200) across the different data sets. In normalizing the read depth, the quality filter 256 can calculate a scale factor for each data set by dividing the predetermined depth by the corresponding sample read depth 214. The scale factor can be applied or multiplied to wild-type counts (e.g., number of character sequences/segments corresponding to genes found in natural non-mutated form) for the set, thereby calculating the normalized wild-type count. Similarly, the quality filter 256 can apply the scale factor to the mutation counts (e.g., indel counts) found in each corresponding set. Accordingly, the wild-type counts and the mutations counts for the different data sets can be normalized to a common predetermined read depth using the scale factor.

Additionally or alternatively, the quality filter 256 can be configured to remove nucleotides having sub-standard quality. For example, the quality filter 256 can be configured to filter out data samples or strings having the sample quality score 216 (FIG. 2), such as the Phred quality score, below a predetermined quality threshold (e.g., 20). The quality filter 256 can replace characters for the substandard nucleotides to a predetermined character (e.g., 'N').

The processing system 102 can further use the comparison correction filter 258 (FIG. 2) to remove computational noise or errors. Even with the reduced number of computations, the number of computations and comparisons may inadvertently introduce false positives. Accordingly, the comparison correction filter 258 can be configured to correct the intermediate data, such as using a Bonferroni correction process. For example, the comparison correction filter 258 can adjust (by, e.g., dividing) a predetermined somatic classification threshold (p-value criteria, such as 0.01) by the number of phrases being processed/compared.

Moreover, the processing system 102 can use the fraction filter 260 (FIG. 2) to remove or adjust for physiological features and/or collection-based features that interfere with the data processing. In some implementations, the fraction filter 260 can be configured to address samples having relatively low numbers of derived phrases (e.g., sample sets having mutant counts less than a predetermined threshold). For example, the fraction filter 260 can include an allelic fraction filter. The allelic fraction for sample/data can be calculated based on dividing the number of derived phrases 510 by a sum of wild-type counts and mutant counts. The fraction filter 260 can classify data/strings as not being somatic when the corresponding allelic fraction values are less than a predetermined threshold (e.g., 0.05).

Figure 7:
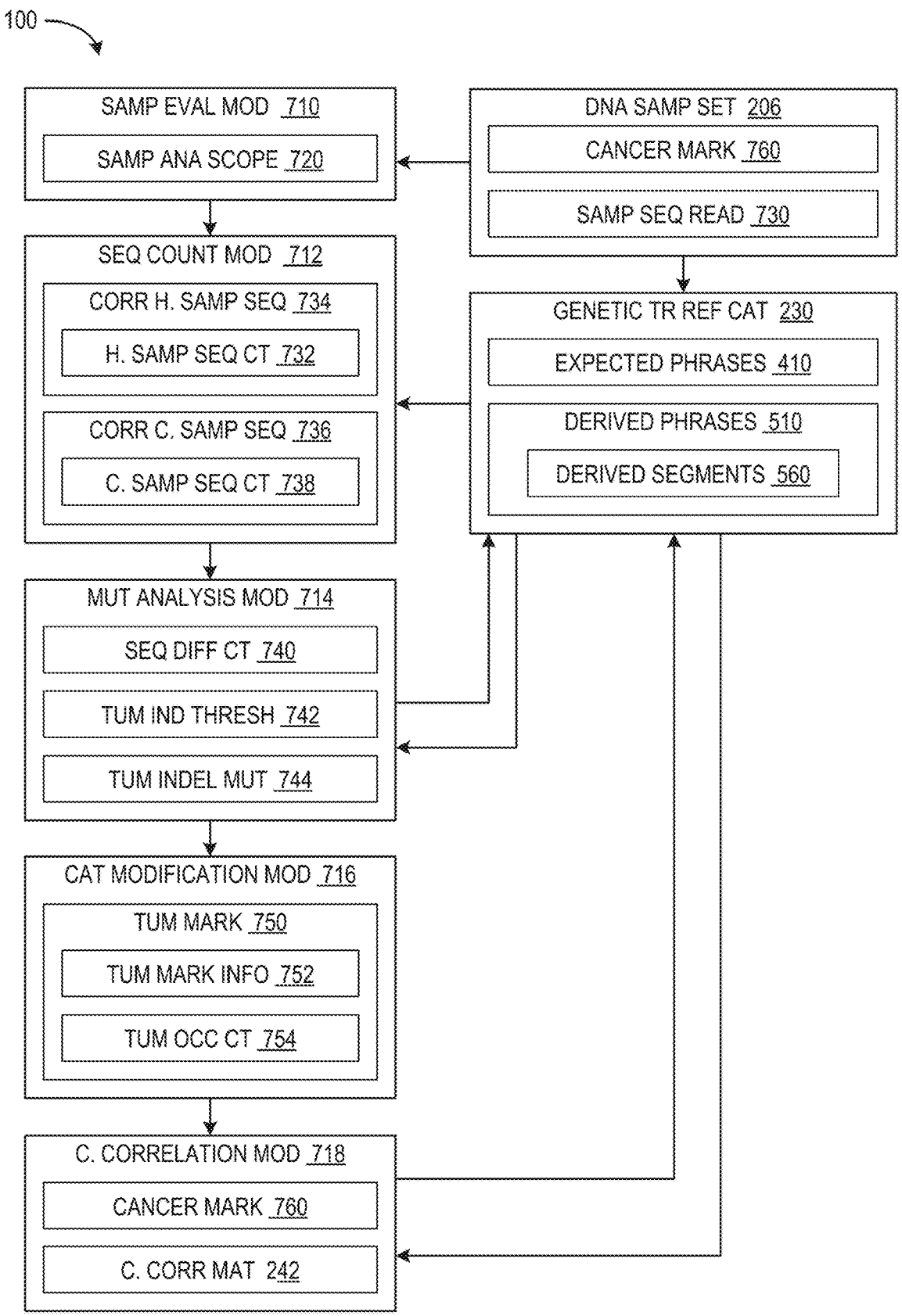
FIG. 7 shows an example control flow diagram illustrating the functions of the system in accordance with one or more implementations of the present technology.

FIG. 7 shows a control flow diagram illustrating the functions of the computing system 100 in accordance with various embodiments. The computing system 100 can be implemented to supplement and refine information in the genome TR reference catalogue 230 with information from the DNA sample sets 206 based on the unique segments 360 and the various phrases. In general, the computing system 100 can analyze one or more of the DNA sample sets 206 to process (1) mutations at specific locations of DNA sequences, (2) correlation of mutation patterns, (3) corresponding indications of one or more types of cancer, or a combination thereof. The functions of the computing system 100 can be implemented with a sample set evaluation module 710, a sequence count module 712, a mutation analysis module 714, a catalogue modification module 716, a cancer correlation module 718, or a combination thereof.

The evaluation module 710 can be configured to evaluate the scope of the DNA sample set 206, including the cancer-free data 210, the non-regional data 211, and/or the cancer-specific data 212. For example, the evaluation module 710 can evaluate the DNA sample set 206 to identify factors, properties, or characteristics thereof to facilitate analysis of the different categories of data. In some implementations, the evaluation module 710 can be optional. The evaluation module 710 can generate a sample analysis scope 720 for the DNA sample set 206. The sample analysis scope 720 is a set of one or more factors that may govern/control the analysis of the DNA sample set 206. For example, the sample analysis scope 720 can be generated based on the supplemental information 220. The sample analysis scope 720 can be used to identify usable phrases (e.g., the expected phrases 410 and/or the derived phrases 510) based on the sequence location 614 and the phrase length k 416.

The computing system 100 can receive the derived phrases 510 and associated information from the genome TR reference catalogue 230 and/or the DNA sample set 206. The mutation analysis mechanism can be implemented with the count module 712 and the analysis module 714. The count module 712 may be responsible for calculating a number of occurrences (e.g., a sequence count) for specific DNA sequences/phrases in a sample set. The count module 712 can calculate the sequence count based on a number of sample sequence reads 730, such as the sequence reads for the DNA fragments in one or more categories of data in the DNA sample set 206.

For the cancer-free data 210, the count module 712 can calculate a healthy sample sequence count 732 for each instance of a corresponding healthy sample sequence 734 identified in the cancer-free data 210. The corresponding healthy sample sequence 734 is a DNA sequence in the healthy sample DNA information 734 that corresponds to one of the derived segments 560 and/or the derived phrases 510. The heathy sample sequence count 732 is the number of times that the corresponding healthy sample sequence 734 is identified in the cancer-free data 210. Similarly, for the cancer-specific data 212 and/or the non-regional data 211, the count module 712 can calculate count values for each instance of a targeted sequence identified in the data group. In other words, the count module 712 can calculate the number of times the various phrases are found within the samples according to the corresponding categories.

The count module 712 can identify the corresponding healthy sample sequence 734 and the corresponding cancerous sample sequence 738 for a given expected phrase, and more specifically the derived phrase. For example, the sequence count module 712 can search through the different categories of data for matches to one or more of the derived segments within the corresponding phrases. As one specific example, the count module 712 can search for a string of consecutive base pairs that matches one of the derived segments 560 of the derived phrases 510.

The count module 712 can calculate the healthy sample sequence count 732 as the total number of each of the corresponding healthy sample sequence 734 identified in each of the sample sequence reads 730 in the cancer-free data 210. In many cases, the corresponding healthy sample sequence 734 will correspond with a single instance of the tandem repeat indel variants 310. In these cases, the total value of the healthy sample sequence count 732 will be equal to the total number of the sample sequence reads 730 in the cancer-free data 210. For example, where the cancer-free data 210 includes 50 instances of the sample sequence reads 730 per DNA segment, the healthy sample sequence count 732 for a given instance of the corresponding healthy sample sequence 734 should also be 50. The case of non-unity between the number of sequencing reads and the healthy sample sequence count 732 can generally be attributed to sequencing errors.

In many cases, the corresponding healthy sample sequence 734 will match with the phrase with the indel variant value 312 of zero (e.g., the expected phrase with no insertions or deletions of the unique segment 360). However, in some cases, the corresponding healthy sample sequence 734 can differ. The differences between the corresponding healthy sample sequence 734 and the phrase with the indel variant value 312 of zero can account for wild type variants (e.g., naturally occurring variations) in the cancer-free data 210.

Similarly, the count module 712 can calculate the cancerous sample sequence count 736 for each of the corresponding cancerous sample sequence 738 that appear in the sample sequence reads 730 in the cancer-specific data 212. Due to possible mutations, the cancer-specific data 212 can include multiple different instances of the corresponding cancerous sample sequence 738 matching different instances of the derived segments 560, with each corresponding cancerous sample sequence 738 having varying values of the cancerous sample sequence count 736. As an example, in some cases, the corresponding cancerous sample sequence 738 and cancerous sample sequence count 736 will match with the corresponding healthy sample sequence 734 and healthy sample sequence count 732, indicating no mutations. As another example, for a given instance of the derived phrase 510, the cancer-specific data 212 may have a split in the cancerous sample sequence count 736 between the cancerous sample sequence 738 that is the same as the corresponding healthy sample sequence 734 and one or more other instances of the indel variants. For a given instance of the derived phrase 510, the count module 712 can track the cancerous sample sequence count 736 for each different instance of the corresponding cancerous sample sequence 738 in the cancer-specific data 212.

The flow can continue to the analysis module 714. The analysis module 714 may be responsible for determining whether a mutation exists in the corresponding cancerous sample sequence 738 of the cancer-specific data 212. In general, the existence of a mutation in the cancer-specific data 212 can be determined based on differences in the repeated TR patterns between the corresponding heathy sample sequence 734 and the corresponding cancerous sample sequence 738. More specifically, a difference in the number of the repeated base unit 356 can represent the existence of an indel mutation (e.g., a mutation corresponding to an insertion or a deletion of the repeated TR unit), such as for cancer-specific data 212 in comparison to the cancer-free data 210. For example, the analysis module 714 can determine that a mutation exists when the corresponding cancerous sample sequence 738 matches one of the derived segments 560 and/or the derived phrases different than that of the corresponding healthy sample sequence 734. In another example, the analysis module 714 can determine the difference between the corresponding healthy sample sequence 734 and the corresponding cancerous sample sequence 738 based on a sequence different count 740 (e.g., the total number of corresponding cancerous sample sequences 738 differing from the corresponding healthy sample sequences 734). In the case where the sequence difference count 740 indicates no differences, such as when the sequence difference count 740 is zero, the analysis module 714 can determine that no mutation exists in the corresponding cancerous sample sequence 738.

In general, the analysis module 714 can determine that an indel mutation has occurred when the sequence difference count 740 is a non-zero value. In some embodiments, the analysis module 714 determines whether the indel mutation is a tumorous indel mutation based on whether the sequence difference count 740 is greater than the error percentage of the approach or apparatus used to sequence the cancer-free data 210, cancer-specific data 212, or a combination thereof.

In another implementation, the analysis module 714 can determine whether the indel mutation is a tumorous indel mutation 744 based on a tumor indication threshold 742. The tumor indication threshold 742 is an indicator of whether the number of mutations for a particular sequence in the cancer-specific data 212 indicates the existence of a tumorous indel mutation 744. The tumorous indel mutation 744 may occur when the sequence difference count 740 exceeds a tumor indication threshold 742. As an example, the tumor indication threshold 742 can be based on a percentage between the total number of sample sequence reads 730 and the sequence difference count 740. As a specific example, the tumor indication threshold 742 can require a sequence different count 740 be greater than 70 percent of the sample sequence reads 730 for the cancer-specific data 212. In another specific example, the tumor indication threshold 742 can require the sequence difference count 740 be greater than 80 percent of the sample sequence reads 730 for the cancer-specific data 212. In another specific example, the tumor indication threshold 742 can require the sequence difference count 740 be greater than 90 percent of the sample sequence reads 730 for the cancer-specific data 212.

When the corresponding cancerous sample sequence 738 includes the tumorous indel mutation 744, the computing system 100 can implement the modification module 716 to update or modify the genome TR reference catalogue 230. Said another way, the computing system 100 can implement the modification module 716 responsive to determining that the corresponding cancerous sample sequence 738 includes the tumorous indel mutation 744. For example, the modification module 716 can modify the genome TR reference catalogue 230 by identifying the instance of the catalogue entries 610 as a tumor marker 750 when the tumorous indel mutation 744 exists in the corresponding cancerous sample sequence 738.

The catalogue entries 610 that are identified as a tumor marker 750 can be modified by the modification module 716 to include tumor marker information 752. Some examples of the tumor marker information 752 can include a tumor occurrence count 754, such as the number of times that the tumorous indel mutation 744 was identified in a particular instance of the segment/phrase (e.g., TR pattern) for a given form of cancer. As a specific example, the tumor occurrence count 754 can be compiled from analysis of the DNA sample sets 206 for numerous cancer patients.

In another example, the tumor marker identification 752 can include information about the different instances of the corresponding cancerous sample sequence 738 matching to different instances of the derived segments/phrases along with the cancerous sample sequence count 736, the total number of sample sequence reads 730 of the DNA sample set 206, all or portions of the supplemental information 220, or a combination thereof. In a further example, the tumor marker information 752 can include the number of repeated base units 356 in the corresponding cancerous sample sequence 738 that were different from the corresponding healthy sample sequence 734.

The tumor marker information 752 can include information based on the supplemental information 220. For example, the tumor marker information 752 can include supplemental information 220 (e.g., source information), such as the cancer type, the stage of cancer development, organ or tissue from which the sample was extracted, or a combination thereof. In another example, the tumor marker information 752 can include the supplemental information 220 of the patient demographic information, such as the age, the gender, the ethnicity, the geographic location of where the patient resides or has been, the duration of time that the patient stayed or resided at the geographic location, predispositions for genetic disorders or cancer development, or a combination thereof.

The computing system 100 can use one or more instances of the segments/phrases identified as the tumor marker 750 to generate the cancer correlation matrix 242 with the correlation module 718. For example, the correlation module 718 can identify cancer markers 760 based on the tumor occurrence count 754 for each of the tumor markers 750 in the genome TR reference catalogue 230. The cancer markers 760 can correspond to mutation hotspots that are specific to indel mutations in instances of the TR patterns. In one implementation, the correlation module 718 can identify the cancer markers 760 based on regression analysis. For example, the regression analysis can be performed with a receiver operating characteristic curve to the optimum sensitivity and specificity from the tumor markers 750, tumor occurrence count 754, or a combination thereof to determine the cancer markers 760.

In another implementation, the correlation module 718 can identify the cancer markers 760 based on a ratio between, or percentage of, the tumor occurrence count 754 for the tumor marker 750 and the total number of the DNA sample sets 206 of a particular form of cancer that have been analyzed for the tumor marker 750. As a specific example, the correlation module 718 can identify the cancer markers 760 as the tumor markers 750 when the ratio between the tumor occurrence count 754 and the total number of DNA sample sets 206 that are analyzed is 90 percent or more of the DNA sample sets 206 for a particular form of cancer. In this case, the cancer correlation matrix 242 can include the cancer markers 760 that were identified in this manner.

In a further implementation, the correlation module 718 generates the cancer correlation matrix 242 as the tumor markers 750 that are common among a percentage of the DNA sample sets 206 for a particular form of cancer are found. For example, the correlation module 718 can generate the cancer correlation matrix 242 as the tumor markers 750 appear in 90 percent or more of the total number of DNA sample sets 206. In other implementations, the correlation module 718 can generate the cancer correlation matrix 242 through other methods, such as regression analysis or clustering.

The correlation module 718 can generate the cancer correlation matrix 242 taking into account the supplemental information 220, such as the patient demographic information, to generate the cancer correlation matrix 242 for sub-populations. For example, the correlation module 718 can generate the cancer correlation matrix 242 based on the patient demographic information specific to gender, nationality, geographic location, occupation, age, another characteristic, or a combination of characteristics.

The computing system 100 has been described in the context of modules that perform, serve, or support certain functions as an example. The computing system 100 can partition or order the modules differently. For example, the evaluation module 710 could be implemented on the processing system 102, while the count module 712, analysis module 714, and correlation module 718 could be implemented on another computing device (also called the "external computing device" or simply "external device") separate from the computing system. Alternatively, the processing system 102 can include the various modules described above.

The computing system 100 can implement the refinement mechanism 115 (FIG. 1A) via one or more or different modules described above. For example, the computing system 100 can include/implement the quality filter 256 in the sample evaluation module 710. Also, the computing system 100 can include/implement the consecutive overlap filter 252 and/or the duplicate filter 254 in the count module 712 (e.g., before or in preparation for the counting operations described above). Moreover, the count module 712 and/or the analysis module 714 can include the comparison correction filter 258 and/or the fraction filter 260.

Figure 8:
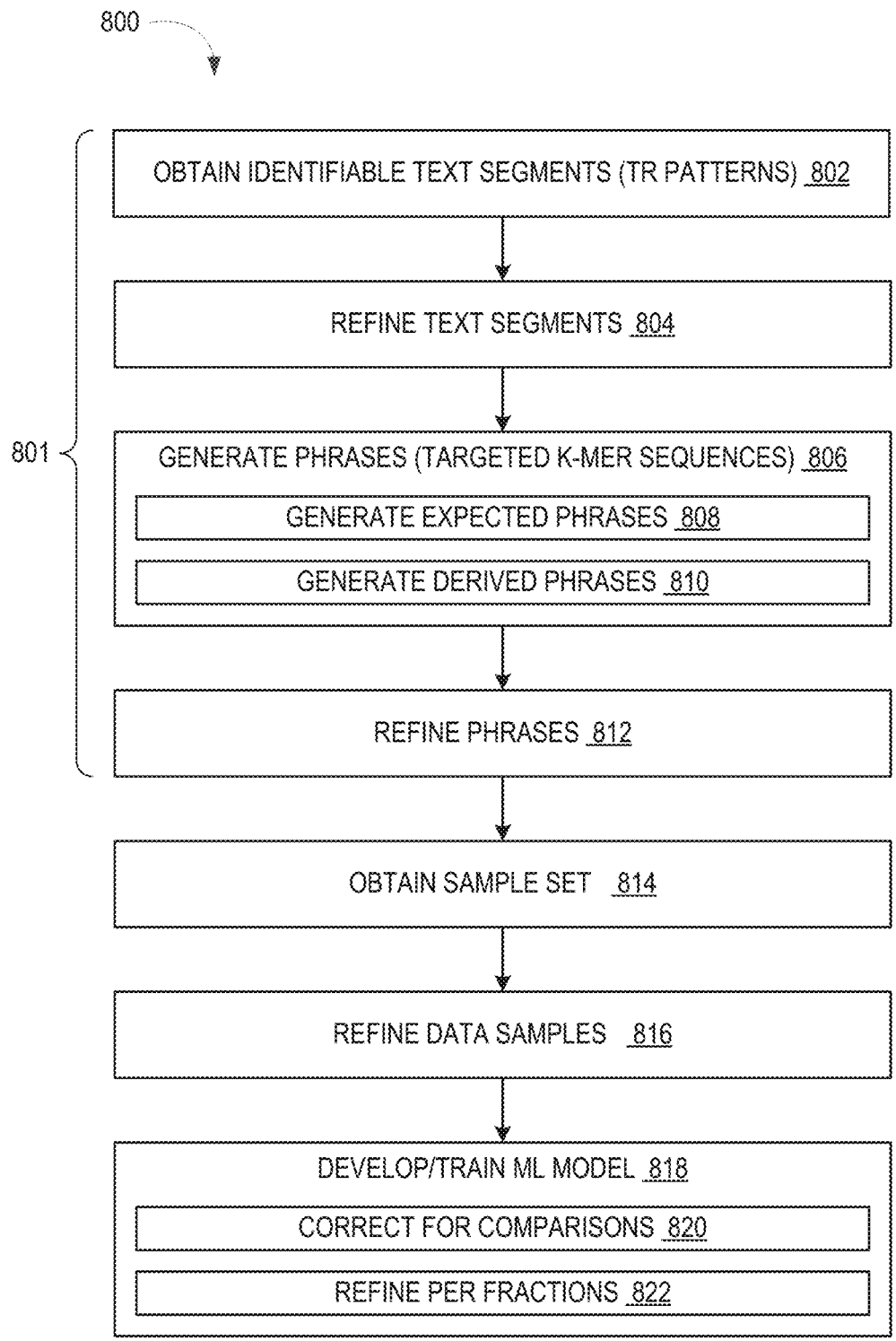
FIG. 8 shows a flow chart of a method for processing and refining DNA-based text data for cancer analysis in accordance with one or more implementations of the present technology.

FIG. 8 shows a flow chart of a method 800 for processing and refining DNA-based text data for cancer analysis in accordance with one or more implementations of the present technology. The method 800 can be implemented using the computing system 100 (FIG. 1A) including the processing system 102 (FIG. 1A). The method 800 can be for developing the ML model 104 (FIG. 1) including generating the various phrases and refining the processing results (via, e.g., the refinement mechanism 115 (FIG. 1)) as described above.

The method 800 includes the computing system 100 obtaining identifiable text sequences (e.g., TR-based patterns) at block 802. In some implementations, the processing system 102 can obtain the identifiable text sequences based on generating the unique segments 360 (FIG. 3) from the reference data 112 (FIG. 1A), such as by generating the character patterns representative of the identifiable TR patterns the human genome. In other implementations, the processing system 102 can access/receive the unique segments 360 generated by an external device.

The obtained unique segments 360 can serve as an initial set of segments representative of TR sequences. Each segment in the initial set can include N number of adjacently repeated base units 356. The repeated base units 356 for the initial set can have the base unit length 424 that is uniform across the segments.

At block 804, the computing system 100 can refine the identifiable text segments, such as by using/implementing the consecutive overlap filter 252 (FIG. 2). In some implementations, the processing system 102 can refine the identifiable text segments by removing the overlaps 352 (FIG. 3A), such as the TR patterns that are consecutive of and/or overlap each other, from the initial set of the unique segments 360 as described above. The processing system 102 can generate a refined set of the segments based on removing the overlaps 352 from the initial set.

At block 806, the computing system 100 can generate the phrases, such as the k-mer sequences targeted for use in subsequent data processing. For example, at block 808, the processing system 102 can generate the expected phrases 410 (FIG. 4). The processing system 102 can use the unique segments 360 (e.g., uniquely identifiable TR patterns) to generate the expected phrases 410, such as by adding different combinations of the flanking text 414 (FIG. 4) as described above. Also, at block 810, the processing system 102 can generate the derived phrases 510 (FIG. 5). The processing system 102 can use the expected phrases 410 to generate the derived phrases 510, such as by adjusting the unique segments 360 within the expected phrases to the derived segments 560 representative of indel mutations as described above.

In some implementations, the generated phrases can serve as an initial set. The generated phrases can correspond to different locations within the human genome. For example, the phrases can have the phrase length k 416 and include (1) location-specific TR-based segments (e.g., expected phrases 410) and/or (2) indel derivations of the TR-based segments adjacent to corresponding sets of flanking texts (e.g., derived phrases 510).

At block 812, the computing system 100 can refine the set of phrases, such as by using/implementing the duplicate filter 254 (FIG. 2). For example, the processing system 102 can refine the expected phrases 410 and/or derived phrases 510 by removing the duplicates or representations of DNA sequences or mutations that may correspond to more than one location. In other words, the processing system 102 can search for inadvertently generated representations of mutations that match mutations or expected/healthy sequences corresponding to a different location in the human genome as described above.

The operations described above for one or more of the blocks 802-812 can correspond to a block 801 for generating text phrases that represent different DNA sequences. The generated text phrases can represent various uniquely identifiable DNA sequences and mutations sequences for TR indel variants. The generated/refined text phrases can be used to determine correlations between the various mutations and onset cancer in the DNA sample set 206.

At block 814, the computing system 100 can obtain one or more sample sets (e.g., the DNA sample set 206 (FIG. 2)). In some implementations, the processing system 102 can receive sequenced DNA data from publicly available databases, healthcare providers, and/or submitting patients. The obtained data sample sets can include corresponding or known diagnoses, such as categorizations or tags identifying that the DNA data is from patients confirmed to be without cancer or confirmed to have specific cancers. Additionally, the obtained data can include physiological source locations of the DNA data. For samples sourced from the patients having cancer, the source locations can be the cancerous tumor or a location different from or unrelated to the malignant tumors. Accordingly, the processing system 102 can include a combination of the cancer-free data 210, the non-regional data 211, and the cancer-specific data 212, illustrated in FIG. 2. The obtained DNA sample set 112 can further include other details, such as the supplemental information 220 (FIG. 2), the sample read depth 214 (FIG. 2), the sample quality score 216 (FIG. 2), or the like.

At block 816, the computing system 100 can refine the data samples 816, such as by using/implementing the quality filter 256 (FIG. 2). For example, the processing system 102 can identify the characters corresponding to nucleotides having Phred scores less than the quality threshold. The processing system 102 can replace the identified characters with a predetermined dummy letter as described above. Additionally or alternatively, the processing system 102 can filter and/or adjust for nonuniform read counts or read depths across the DNA sample set 206. The processing system 102 can remove sample data having the sample read depth 214 below a depth requirement/threshold as described above. The processing system 102 can also adjust for the nonuniformity by calculating and applying the scale factor to the read counts as described above.

At block 818, the computing system 100 can develop and train the ML model 104 using the refined phrases and the refined data samples. For example, the processing system 102 can count and analyze the various somatic mutations, compute correlations between the mutations and cancers, and the like as described above. Using the results, the processing system 102 can select a set of features that include phrases having sufficient correlations to one or more types of cancers. The processing system 102 can design and train the ML model 104 using the selected features (e.g., correlative phrases representative of cancer-causing somatic mutations).

In developing and training the ML model 104, the processing system 102 can further refine the intermediate processing results. For example, at block 820, the processing system 102 can correct for comparison noises, such as by using/implementing the comparison correction filter 258 (FIG. 2). The processing system 102 can correct for the comparison noises using the p-value criteria as described above. Also, at block 822, the processing system 102 can refine the intermediate results per the fractional features. The processing system 102 can use the fraction filter 260 (FIG. 2) in classifying or distinguishing between somatic and non-somatic mutations.

The processing system 102 can develop/train the ML model 104 such that the model is configured to compute a cancer signal based on analyzing text-based patient DNA data according to represented somatic indel mutations in patient DNA. The processing system 102 can develop/train the ML model 104 based on computing correlations between mutations (as represented by the derived phrases) and onset/existence of one or more types of cancers as represented by the DNA sample set 206. Using the correlations, the ML model 104 can be configured to compute the cancer signal that represents (1) a likelihood that a corresponding patient has developed the one or more types of cancer, (2) a likelihood that the patient will develop the one or more types of cancer within a given duration, and/or (3) a development status at least leading up to onset of one or more types of cancer.

Approaches to Selecting Features for Improved Cancer Detection

In one aspect, the present disclosure is directed toward AI and ML mechanisms that can be used to select features for detecting cancer through analysis of genetic information. For the purposes of illustration, embodiments may be described in the context of a DNA sample set (e.g., DNA sample set 206) that includes genetic information in the form of DNA sequences that are associated with, or representative of, cancer-free data 210, non-regional data 211, and/or cancer-specific data 212. Said another way, the DNA sample set may include genetic information generated for a cancer-free sample, a sample taken from a non-cancerous region, or a cancerous sample.

At a high level, the approach described above involves obtaining data that includes (i) DNA sequences (e.g., in the form of cancer-free data 210 or non-regional data 211) corresponding to non-cancerous samples and (ii) DNA sequences (e.g., in the form of cancer-specific data 212) corresponding to cancerous samples. The former may be referred to as "non-cancerous DNA sequences" or "reference DNA sequences," and the latter may be referred to as "cancerous DNA sequences." Moreover, because this data is to be used in the training of the ML model 104, this data may be referred to as a "training dataset." The training dataset can be processed by a computing system (e.g., computing system 100 of FIG. 1A)—and more specifically, a processing system (e.g., processing system 102 of FIG. 1A)—to identify an initial set of unique segments 360 (FIG. 3B) and corresponding segment locations 364 (FIG. 3B) that identify positions (e.g., first letter positions) of the segments within a target sequence 354 (FIG. 3B) as discussed above. Each unique segment 360 may be representative of a sequence of nucleotides that uniquely corresponds to a molecular position within the human genome.

The computing system 100 can process the training dataset according to unique locations or markers. For example, the computing system can generate a list of unique TR-based patterns and indel variants thereof based on an analysis of flanking sequences (e.g., by examining leading nucleotides and trailing nucleotides) using a "sliding window approach." In particular, a "sliding window" that has a predetermined width (e.g., defined by phrase length k 416 of FIG. 4) may be used to isolate successive portions within an expected phrase 410 that is representative of a DNA sequence. As the computing system 100 shifts the bounds of the sliding window, the information contained within the sliding window can be compared to a reference pattern (e.g., human genome or portions thereof) to verify target conditions, such as uniqueness across the human genome. When the target conditions are verified, the computing system 100 can retain the information within the sliding window as uniquely identifiable TRs. The computing system 100 can further process the uniquely identifiable TRs to identify potential mutations (e.g., indels that add to or delete from the sequence of interest). The computing system 100 can process and retain a set of potential mutations that may be unique and/or indicative of certain types of cancer.

As part of training or implementing the ML model 104, a DNA sample set 206 that includes DNA data (e.g., representative of a set of sequenced DNA information) can be provided as input, for analysis in accordance with the uniquely identifiable TRs and/or indel variants thereof. In other words, the computing system 100 can use the uniquely identifiable TRs and/or indel variants thereof to analyze the DNA data included in the DNA sample set 206. As mentioned above, the DNA sample set 206 can include genetic information (e.g., text-based representations) derived or extracted from human bodies. Thus, the computing system 100 can develop, train, or implement the ML model 104 based on analyzing instances or patterns of the uniquely identifiable TRs and/or variants thereof in relation to certain types of cancers. The locations of detected deviations and/or the patterns of detected deviations within the DNA data of the DNA sample set 206 may be aggregated to identify an initial set of indicators configured to predict onset of cancer, identify a likely onset of the predicted type(s) of cancer, detect existence and/or absence of cancer, identify the existing type(s) of cancer, or a combination thereof.

Figure 9:
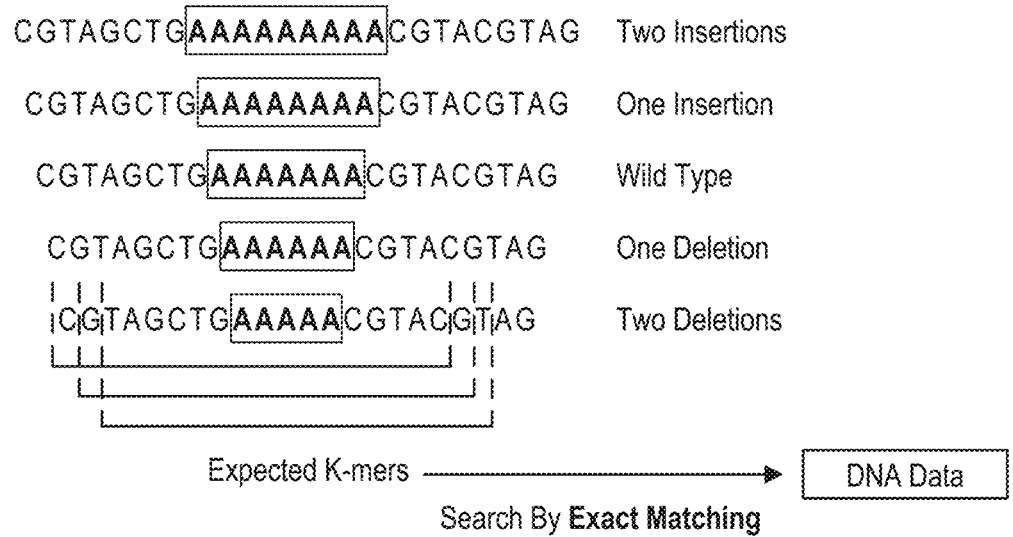
FIG. 9 (SEQ ID NO: 13-17) illustrates how the computing system can flexibly search for TR sequences with different indel mutations in expected phrases in accordance with one or more implementations of the present technology.

FIG. 9 illustrates how the computing system 100 can flexibly search for TR sequences with different indel mutations in expected phrases 410. As mentioned above, the expected phrases 410 may also be referred to as "k-mers." At a high level, a TR sequence is a segment of a longer sequence that includes multiple repeated patterns that exceed a minimum number of base pairs. For example, each TR sequence can be selected based on the repeated base unit having the minimum number of base pairs ranging between five and eight base pairs.

In FIG. 9, the unique segment that is representative of the TR sequence has seven base pairs with a repeated base unit of one base pair 'A.' As such, an indel mutation of one deletion will result in a unique segment that has six base pairs with a repeated base unit of 'A' while an indel mutation of two deletions will result in a unique segment that has five base pairs with a repeated base unit of 'A.' similarly, an indel mutation of one insertion will result in a unique segment that has eight base pairs with a repeated base unit of 'A' while an indel mutation of two insertions will result in a unique segment that has nine base pairs with a repeated base unit of 'A.' It should be appreciated that these examples are shown solely for the purpose of illustration. Indel variants with more than two insertions or deletions could be part of the expected phrases 410.

Through the use of expected phrases 410 or "k-mers," the computing system 100 can determine sequences of a given length (e.g., at least length n, where n is an integer greater than two) and then count the occurrences of the TR sequences and indel variants of interest. For example, the computing system 100 may parse reference data (e.g., reference data 112 of FIG. 1A) to discover the number of occurrences of a given TR sequence in sequencing reads corresponding to a non-cancerous sample (e.g., of tissue, bodily fluid, etc.).

Some challenges with mutation calling can be addressed by using the k-mers instead. First, mutation calling can be based on the human genome—which serves as a reference—rather than a patient-specific genome. Calculating all possible indel variants for a TR sequence across the human genome offers a flexible, reference-free approach to mutation calling. Second, the k-mers can be defined to cover sequences (e.g., corresponding to indel variants) that vary slightly from a TR sequence of interest as discussed above, allowing for more reliable mutation calling. This allows the computing system 100 to experience fewer errors in detecting TR sequences and indel variants thereof due to amplification issues, alignment issues, or the like. Simply put, relying on TR sequences and indel variants determined in the manner prescribed above lessens the likelihood of inaccuracy, for example, due to false positives or false negatives.

In samples taken from a human body, satellite DNA known as "msDNA" may be present. At a high level, msDNA is a complex of DNA, RNA, and possibly proteins that can be found in fluids like blood. msDNA can comprise a small, single-stranded DNA molecule that is linked to a small, single-stranded RNA molecule. One of the benefits of employing k-mers is that msDNA could be examined in addition to, or instead of, amplified DNA molecules. Through examination, the computing system 100 can identify the number of instances of each k-mer in a DNA sample set 206 regardless of its form. In particular, the computing system 100 can search the DNA sample set 206 by exact matching each k-mer against the DNA data included therein. At a high level, each target location included in the initial set of unique segments 360 can identify a molecular position.

As mentioned above, the mutations discovered by matching the k-mers against DNA data can be used to create, generate, or otherwise obtain target locations within the human genome. The DNA data could be associated with a single DNA sample set (and thus, a single patient), or the DNA data could be associated with multiple DNA sample sets (and thus, multiple patients). For example, the DNA data may be representative of genetic information corresponding to samples that were collected, characterized, and analyzed by a third party, such as a healthcare system or a research institution (e.g., The Cancer Genome Atlas), for a set of patients (e.g., several hundred or thousand patients). In such a scenario, each DNA sample set may be associated with the genetic information of a corresponding patient and a label that either indicates (i) the type of cancer with which the corresponding patient was diagnosed or (ii) that the patient was diagnosed as not having cancer. Through analysis of the DNA data, the computing system can establish a unique segment set 113 (FIG. 1A) as discussed above.

In some implementations, the computing system 100 uses a refinement mechanism 115 (FIG. 1A) to reduce the size of the unique segment set 113 to produce a refined set 116. For example, the computing system 100 may apply the refinement mechanism 115 to reduce the number of expected phrases 120 and derived phrases 122 that collectively correspond to the unique segment set 113, for example, by removing duplicate phrases and overlap phrases. By removing duplicate phrases and overlap phrases, the computing device 100 can avoid duplicative processing, namely, where the unique segment set 113 would indicate to look for instances of a given phrase at the same location or slightly different locations. By implementing the refined set 116 instead of the unique segment set 113, computational resources can be conserved (and issues such as duplicative processing, noise, and the like can be avoided).

However, the number of phrases (and therefore, target locations) included in the refined set 116 can still be quite large. For example, if the computing system 100 employs the sliding window approach described above to identify mutations in DNA data, the computing system 100 may identify tens or hundreds of thousands of instances of the expected phrases 120 and derived phrases 122 that are included in the refined set 116. Training the ML model 104 to detect cancer using these instances and corresponding locations requires meaningful amounts of time and computational resources due to the sheer volume of information. Similarly, implementing a version of the ML model 104 that has been trained to examine the wide range of locations for the expected phrases 120 and derived phrases 122 may require meaningful amounts of time and computational resources. Simply put, training the ML model 104 using the entire refined set 116 may be incredibly resource intensive during the training and inferencing stages, and it can also result in overfitting as the ML model 104 can be informed by too many features—making the ML model 104 too flexible.

Embodiments of the technology described below reduce the number of locations at which the ML model 104 is trained to search for instances of the expected phrases 120 and derived phrases 122 that are included in the refined set 116, thereby improving the efficiency of the computing system 100 overall. For example, the training stage is simplified as the amount of training data is lessened, and the inferencing stage is simplified as the ML model 104 can more quickly search a smaller number of locations. Further details are provided below.

FIG. 10 includes a table that illustrates how the number of locations at which to search can quickly expand as the number of samples (and thus, features) increases. In FIG. 10, the values correspond to DNA sample sets acquired from The Cancer Genome Atlas (TCGA). These DNA sample sets are collectively representative of genetic information that can serve as training data for the ML model 104. As shown in FIG. 10, the genetic information corresponds to 33 different types of cancer selected for study by TCGA, and each type is associated with "healthy" samples and/or cancerous samples. The "healthy" samples may be representative of cancer-free data 210 or non-regional data 211, while the cancerous samples may be representative of cancer-specific data 212. The different types of cancer include adrenocortical carcinoma (ACC), bladder urothelial carcinoma (BLCA), breast invasive carcinoma (BRCA), cervical squamous cell carcinoma and endocervical adenocarcinoma (CESC), cholangiocarcinoma (CHOL), colon adenocarcinoma (COAD), lymphoid neoplasm diffuse large B-cell lymphoma (DLBC), esophageal carcinoma (ESCA), glioblastoma multiforme (GBM), head and neck squamous cell carcinoma (HNSC), kidney chromophobe (KICH), kidney renal clear cell carcinoma (KIRC), kidney renal papillary cell carcinoma (KIRP), acute myeloid leukemia (LAML), lower grade glioma (LGG), liver hepatocellular carcinoma (LIHC), lung adenocarcinoma (LUAD), lung squamous cell carcinoma (LUSC), mesothelioma (MESO), ovarian serous cystadenocarcinoma (OV), pancreatic adenocarcinoma (PAAD), pheochromocytoma and paraganglioma (PCPG), prostate adenocarcinoma (PRAD), rectum adenocarcinoma (READ), sarcoma (SARC), skin cutaneous melanoma (SKCM), stomach adenocarcinoma (STAD), testicular germ cell tumors (TGCT), thyroid carcinoma (THCA), thymoma (THYM), uterine corpus endometrial carcinoma (UCEC), uterine carcinosarcoma (UCS), and uveal melanoma (UVM). The exact number of samples associated with each type is not germane. However, the number of samples across the different types illustrates how training the ML model 104 can quickly become burdensome.

Introduced here, therefore, is an approach to further analyzing the unique segment set 113, initial analysis set 114, or refined set 116, for example, via ML mechanisms such as SVMs, neural networks, random forests, or logistic models that employ logistic regression, to identify a reduced set of locations at which to search. For simplicity, the unique segment set 113, initial analysis set 114, or refined set 116 may be called the "initial set," "expanded set," or "first set," and the reduced set of locations may be called the "reduced set," "optimized set," or "second set." Moreover, the locations included in the reduced set may be referred to as "features" that can be examined by the ML model 104 (e.g., for training purposes or inferencing purposes).

Preferably, the reduced set should be selected, identified, or otherwise determined so as to provide at least a threshold amount of contribution, as measured by metrics such as accuracy, precision, recall, specificity, F1, sensitivity, and the like, in providing a diagnosis based on analysis of a DNA data. Said another way, reduction of the unique segment set 113, initial analysis set 114, or refined set 116 should be done intelligently and strategically to ensure that while the total number of locations searched by the ML model 104 is lessened, the accuracy remains high. Simply put, the goal of reduction should be to eliminate those locations that are unlikely to have a significant impact on the ability of the ML model 104 to render diagnoses through analysis of DNA data.

There are several benefits to the approach further described below. Notably, the reduced set can be used to reduce the volume of training data to be used to train the ML model 104 to detect cancer through analysis of DNA data, thereby increasing the speed of model development and lessening the amount of computational resources needed for model development. This benefit is similarly applicable to implementation of the ML model 104 following training. Because the ML model 104 is trained using a smaller set of features, the ML model 104 can make predictions regarding the absence or presence of cancer in a more time- and resource-efficient manner.

It has been found that the approach further described below exhibits several notable advantages over traditional methodologies for training, namely:

First, the ability to reduce tens or hundreds of thousands of locations down to several thousand target locations (e.g., a reduction by a factor of 3, 5, 10, or more) for various analyses (e.g., single classifier for a single type of cancer, multi-classifier for multiple types of cancer, or the like). For (i) detection of each type of cancer and/or (ii) an overall determination of existence of cancer, the computing system 100 can generate a respective reduced set of locations. Accordingly, the computing system 100 may generate multiple reduced sets via reduction of multiple expanded sets, each of which is associated with a different one of multiple types of cancer. Alternatively, the computing system 100 may generate a reduced set via reduction of an expanded set that includes locations associated with multiple types of cancer. As such, the computing system 100 may not need to examine the entire expanded set of locations for each type of cancer for which a diagnosis is to be rendered. This is particularly important if the ML model 104 is designed to account for the presence of a large number of different cancer types (e.g., the 33 cancer types listed in FIG. 10 for which DNA data is available from TCGA).

Second, high metrics (e.g., accuracy, precision, recall, sensitivity, specificity, and localization) can be maintained for the ML model 104—indicating that performance is good—regardless of the number of cancer types for which diagnoses are to be rendered. Assume, for example, that the computing system 100 acquires DNA data (e.g., from TCGA or a healthcare system) regarding thousands of patients diagnosed with various types of cancer. In such a scenario, the computing system 100 can produce an initial set of locations and then reduce—on a per-cancer-type basis—the initial set to create multiple reduced sets, each of which is associated with a different one of the various types of cancer. Referring to FIG. 10, for example, the computing system 100 may create 33 reduced sets, each of which includes locations at which to search for evidence of a corresponding one of the 33 different types of cancer. This reduction can be performed in an independent manner to ensure that high metrics can be maintained for each type of cancer.

Figure 11:
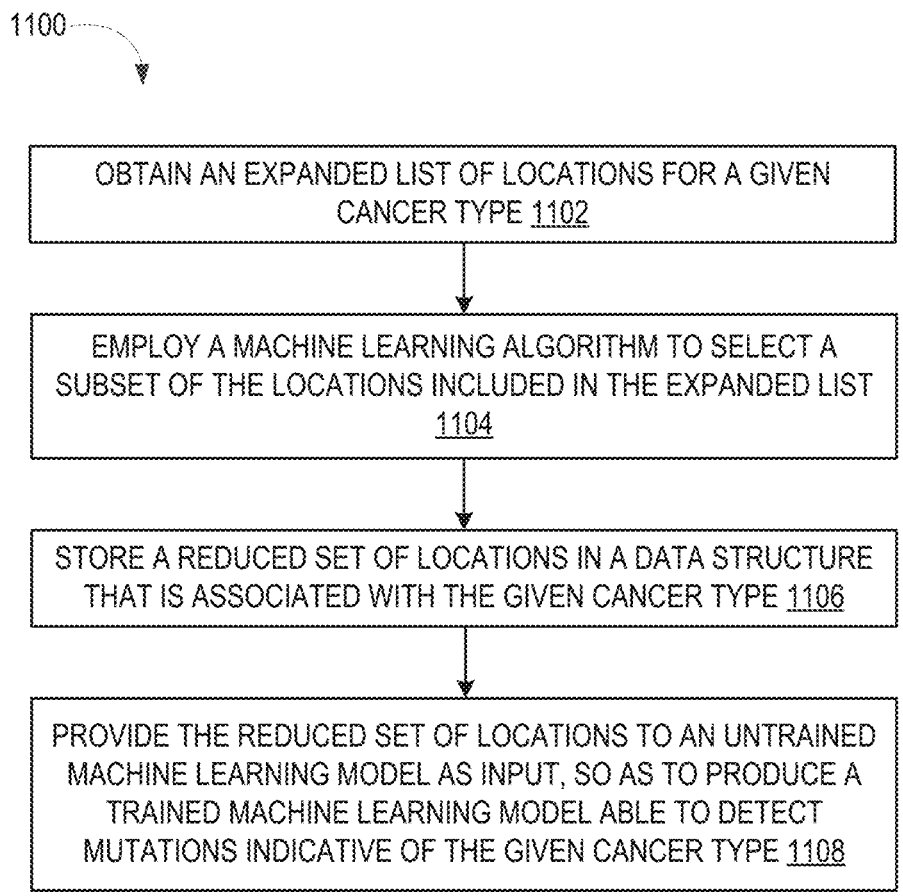
FIG. 11 includes a flow chart of a method for reducing an expanded set of locations, so as to create a reduced set of locations at which to search for abnormalities in accordance with one or more implementations of the present technology.

FIG. 11 includes a flow chart of a method 1100 for reducing an expanded set of locations, so as to create a reduced set of locations at which to search for abnormalities. As mentioned above, this reduced set of locations can be used to train the ML model 104 to search for abnormalities at specific locations where mutations are indicative of either the presence of cancer or the potential onset of cancer. Said another way, this reduced set of locations may indicate the molecular positions at which to search for abnormalities that are indicative of mutations. For the purpose of illustration, the method 1100 is described as being performed by the computing system 100. However, those skilled in the art will recognize that the method 1100 could be implemented by the various modules described above with respect to FIG. 7.

At block 1102, the computing system 100 can obtain an expanded list of locations for a given cancer type. For example, the computing system 100 may employ a sliding window approach to create, based on comparisons of DNA data associated with individuals known to have the given cancer type to the reference human genome, a unique segment set 113. The computing system 100 can use the unique segment set 113 to generate the initial analysis set 114. For example, the computing system 100 may generate the initial analysis set 114 by identifying expected phrases 120 that include the unique segment set 113 and/or by computing derivations thereof (e.g., derived phrases 122) that represent mutations targeted for analysis. As mentioned above, the computing system 100 may employ a refinement mechanism 115 that, in operation, processes the unique segment set 113 and/or the initial analysis set 114 to generate a refined set 116. Any of the unique segment set 113, initial analysis set 114, or refined set 116 could be representative of the expanded list.

At block 1104, the computing system 100 can employ an ML algorithm to select a subset of the locations included in the expanded list. As an example, the computing system 100 may utilize logistic regression to identify those locations included in the expanded list that are most diagnostically relevant, and therefore most predictive in terms of diagnosing cancer. Alternatively, the computing system 100 may utilize linear regression, a neural network, a decision tree, an SVM algorithm, a Naïve Bayes algorithm, a k-nearest neighbors (KNN) algorithm, a k-means algorithm, a random forest algorithm, a dimensionality reduction algorithm, or the like. Each of the locations may be representative of a feature that can be used to train the ML model 104. Each location included in the expanded list may be deemed diagnostically relevant to some degree based on its discovery within DNA data associated with individuals known to have cancer. However, some locations may be more diagnostically relevant than other locations. Determinations of diagnostic relevance may be based on whether a given location is highly correlated with the targeted analysis (e.g., a positive diagnosis of the given cancer type). For example, locations that are more highly correlated with positive diagnoses of a given cancer type may be identified, by the ML algorithm, as more diagnostically relevant in determining predictions for the given cancer type. In some embodiments, the selected subset of features is used in another operation, such as for whole-genome sequencing, targeted sequencing (e.g., as part of a gene panel), or designing probes, primers, and the like.

Specifically, the computing system 100 can apply an ML algorithm that examines each feature included in the expanded list and then produces a score that is indicative of the importance in producing a diagnostically relevant and accurate output. For example, the score may be indicative of accuracy, precision, recall, sensitivity, specificity, localization, or any combination thereof. Note that, in some embodiments, the computing system 100 can produce, for each feature, multiple scores that are representative of different metrics. The multiple scores could be produced by a single ML algorithm, or each of the multiple Accordingly, the computing system 100 may produce a series of scores, where the number of scores is identical to the number of locations included in the expanded list. Then, the computing system 100 can retain the n highest scoring features, where n is an integer. In some embodiments, the value of n is predetermined. For example, the computing system 100 may retain the 1,000, 2,500, 5,000, 10,000, or 25,000 locations having the highest scores. In other embodiments, the value of n is determined dynamically. For example, the computing system 100 may retain all locations whose scores exceed a predetermined threshold, or the computing system 100 may retain whatever number of locations are necessary to ensure that accuracy of the ML model 104 to be trained remains above a predetermined threshold. Accordingly, the computing system 100 may be responsible for autonomously determining which locations included in the expanded set to discard as not being sufficiently relevant from a diagnostic perspective. Further approaches to discovering the locations that are most predictive of cancer through systematic analysis are described below with reference to FIG. 13.

In some embodiments, the computing system 100 considers each location in the expanded list on its own. Thus, the computing system 100 may determine the importance of a first location, determine the importance of a second location, determine the importance of a third location, etc. Thereafter, the computing system 100 may sort the locations included in the expanded list based on importance and then determine which locations to retain and which locations to discard. In other embodiments, the computing system 100 can iteratively work its way through the expanded list in a combinatorial manner. For example, the computing system 100 may select a first location, determine the importance of the first location, selecting a second location, determining the importance of the second location on its own and in combination with the first location, and so on. Such an approach ensures that the computing system 100 does not discard locations that are diagnostically relevant when considered in combination with other locations. The computing system 100 could employ various ML algorithms to try different permutations of locations included in the expanded set.

Normally, multiple instances of the method 1100 are performed by the computing system 100 for different cancer types. Assume, for example, that the computing system 100 obtains DNA data corresponding to several thousand patients, each of whom has been diagnosed with one of multiple cancer types. For each of the multiple cancer types, the DNA data may include cancer-free data 210, non-regional data 211, and/or cancer-specific data 212 for one or more patients.

For a given cancer type, the computing system 100 may generate an expanded set of locations based on an analysis of the corresponding DNA data as discussed above. In some embodiments, multiple expanded sets are generated through independent analysis of the DNA data associated with each of multiple patients that are known to have the given cancer type. In such a scenario, the computing system 100 may independently reduce each of the multiple expanded sets to generate multiple reduced sets and then combine the multiple reduced sets to form a combined reduced set. In other embodiments, a single expanded set is generated through analysis of all DNA data related to the given cancer type, regardless of the number of patients with which that DNA data is associated. For example, the computing system 100 may combine multiple expanded sets generated through independent analysis of the DNA data associated with each of multiple patients that are known to have the given cancer type, so as to produce a combined expanded set. Then, the computing system 100 may reduce the combined expanded set as discussed above. Accordingly, the computing system 100 may develop a single combined reduced set or multiple reduced sets that can be used to train the ML model 104. Regardless of its approach, the computing system 100 can perform the method 1100 so as to generate at least one reduced set of locations for each cancer type of interest.

At block 1106, the computing system 100 can store the reduced set of locations in a data structure that is associated with the given cancer type. Generally, this reduced set of locations is provided by the computing system 100 to an untrained ML model as input, so as to produce the trained ML model 104, as shown at block 1108. Upon being applied to DNA data associated with a patient whose health state is unknown, the ML model 104 can produce an output that is indicative of a proposed diagnoses for the given cancer type.

The nature of the output may depend on the nature of the reduced set of locations that serves as training data. In embodiments where the ML model 104 is trained using at least one reduced set of locations for each of multiple cancer types, the output produced by the ML model 104 may be binary (e.g., "cancer" or "no cancer," "positive diagnosis" or "negative diagnosis"). Although the ML model 104 may be trained using reduced sets of locations generated for different cancer types, the ML model 104 may be unable to distinguish between the different cancer types. As an example, a given molecular position may be included in the reduced set of locations generated for a first cancer type and the reduced set of locations generated for a second cancer type. If the ML model 104 discovers that a mutation exists at the given molecular position, then the output may simply indicate that cancer is likely.

Additional steps could also be performed. Assume, for example, that the computing system 100 receives input indicative of a request to apply the ML model 104 to DNA data associated with a patient whose health state is unknown. In such a scenario, the computing system 100 can apply the ML model 104 to the DNA data, so as to produce an output that indicates whether the patient is determined to have a given cancer type. At a high level, this output may be based on whether the ML model 104 discovers mutations at the locations included in the reduced set generated for the given cancer type. Then, the computing system 100 can cause display of a visual indicium of the output. For example, the computing system 100 may post a proposed diagnosis to an interface that is accessible to the patient or a healthcare professional who is responsible for caring for the patient. Generally, the proposed diagnosis is not intended to be conclusive, however. Instead, the proposed diagnosis may be intended to prompt further action by the patient or healthcare professional. If, for example, the proposed diagnosis is a positive diagnosis for the given cancer type, then the interface may include an instruction to seek further treatment (e.g., from an oncologist).

In some embodiments, the method 1100 is performed multiple times, such that multiple ML models are trained. Each of the multiple ML models may be trained using a different reduced set of locations. By comparing the ability of the multiple ML models to produce appropriate outputs (e.g., in terms of accuracy of proposed diagnoses), the computing system 100 can determine how best to reduce the set of locations. Thus, the computing system 100 could determine a set of reduced locations that offers the same or comparable accuracy as the original set of locations, by iteratively training the ML model with different sets of reduced locations.

Figure 12:
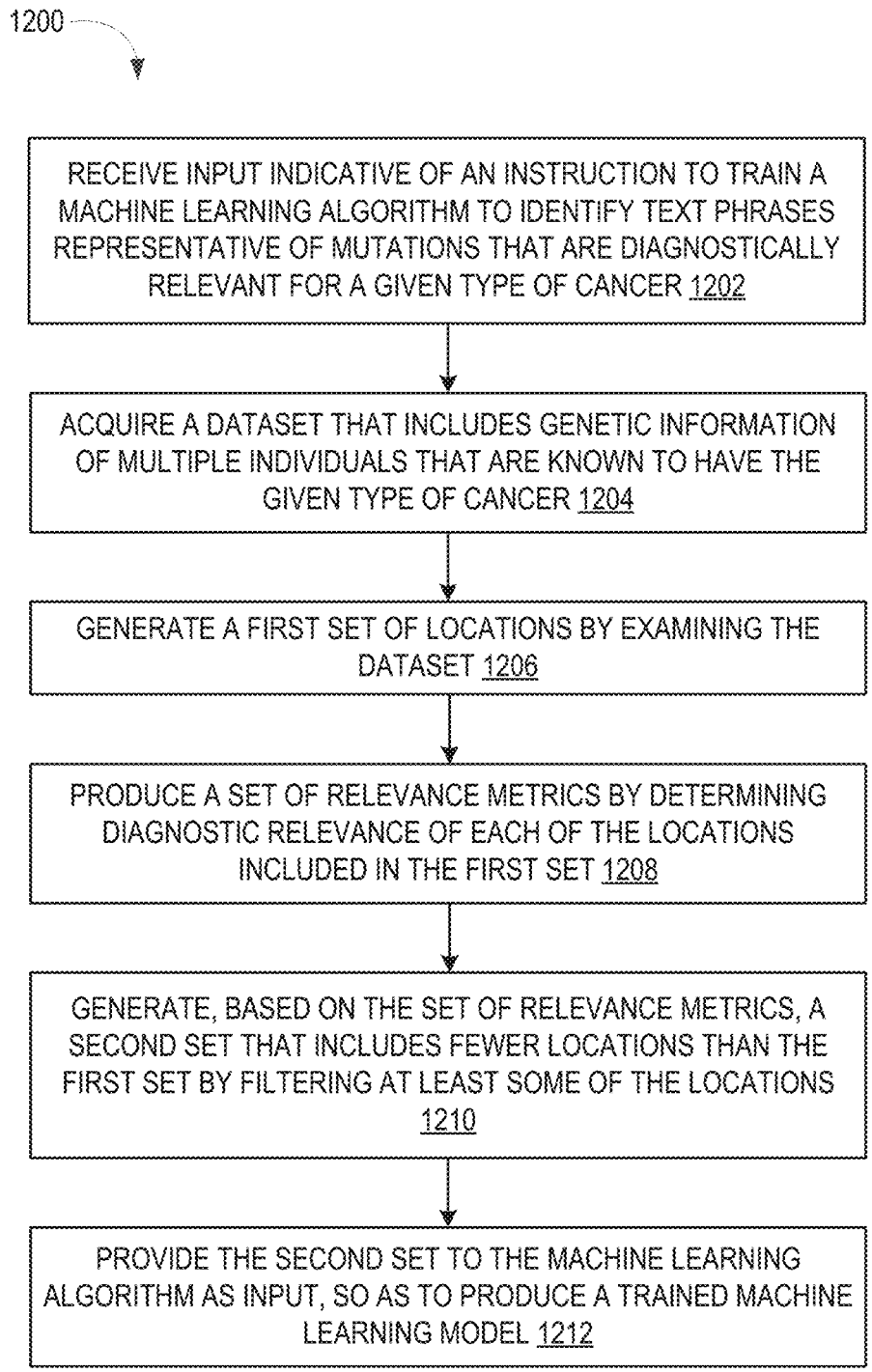
FIG. 12 includes a flow chart of a method for producing a filtered set of features to be used for training in accordance with one or more implementations of the present technology.

FIG. 12 includes a flow chart of a method 1200 for producing a filtered set of features to be used for training. For the purpose of illustration, the method 1200 is described in the context of training a neural network. However, those skilled in the art will recognize that the method 1200 may be similarly applicable to other types of ML model as discussed above.

At block 1202, the computing system 100 can receive input indicative of an instruction to train a machine learning algorithm neural network to identify text phrases that are representative of mutations that are diagnostically relevant for a given type of cancer. For the purpose of illustration, the method 1200 is described in the context of a neural network. However, those skilled in the art will recognize that other machine learning algorithms could be used. As discussed above, each of the text phrases may be representative of a different set of characters, each of which is representative of a nucleotide. Using the text phrases, the computing system 100 can identify patterns, such as TRs and derivations thereof, that are indicative of mutations.

At block 1204, the computing system 100 can access a dataset that includes genetic information of multiple individuals that are known to have the given type of cancer. For example, the computing system 100 may read the data included in the dataset, though the dataset may remain stored on a network-accessible source that is not part of the computing system. As another example, the computing system 100 may initiate a connection with a network-accessible source of genomic data and then cause the dataset to be downloaded from the network-accessible source. In some embodiments, the dataset is in the form of a plain text file (e.g., an ASCII file). In other embodiments, the dataset is in the form of a BAM file or CRAM file. The term "BAM file" is commonly used to refer to the binary version of a tab-delimited text file that contains sequence alignment file, while the term "CRAM file" is commonly used to refer to a compressed version of a BAM file. In embodiments where the computing system 100 accesses or obtains a BAM file or CRAM file, the genetic information included therein may still be described as "text phrases" or "characters," even though those files may not include characters per se.

The computing system 100 may perform these steps in response to receiving the input, for example, that is provided through an interface generated by, or accessible via, the computing system 100. The network-accessible source may be associated with a healthcare system or another entity such as an insurer or a research institution (e.g., TCGA). The genetic information may be representative of the reference data 112 in its "raw form," or the genetic information may be representative of multiple DNA sample sets 206 associated with the multiple individuals.

At block 1206, the computing system 100 can generate a first set of locations by examining the dataset. This first set of locations may be representative of the expanded set mentioned above. Each of the locations included in the first set may be representative of a different molecular position at which a mutation is discovered through analysis of the genetic information. Said another way, each location included in the first set can identify a molecular position at which to search for a mutation that is indicative of cancer. As discussed above, these mutations may be discovered via a sliding window approach in which the genetic information is searched for instances of certain text phrases.

At block 1208, the computing system 100 can produce a set of relevance metrics by determining the diagnostic relevance of each of the locations included in the first set. This can be accomplished in various ways. For example, for each of the locations included in the first set, the computing system 100 may determine a degree of correlation with positive diagnoses of the multiple individuals and compute the corresponding relevance metric based on the degree of correlation. As another example, for each of the locations included in the first set, the computing system 100 may apply an ML algorithm (e.g., the neural network to be trained) that outputs a score indicative of importance in producing a diagnostically accurate output. Each score may be indicative of accuracy, precision, recall, sensitivity, specificity, localization, or any combination thereof. Moreover, each score output by the ML algorithm may be representative of the relevance metric produced for the corresponding location. Thus, for each of the locations included in the first set, the computing system 100 may determine the corresponding relevance metric based on the corresponding score output by the ML algorithm. As another example, for each of the locations included in the first set, the computing system 100 may apply multiple ML algorithms that output multiple scores that are indicative of different metrics. In such embodiments, the computing system 100 can determine the corresponding relevance metric for each of the locations included in the first set based on the multiple scores output by the multiple ML algorithms.

At block 1210, the computing system 100 can generate, based on the set of relevance metrics, a second set that includes fewer locations than the first set by filtering at least some of the locations. Again, this can be accomplished in various ways. For example, the computing system 100 may arrange, based on the set of relevance metrics, the locations included in the first set in sequential order from most diagnostically relevant to least diagnostically relevant, implement a clustering algorithm to discover groupings of the locations, and identify a first grouping and a second grouping that are separated by at least a predetermined amount. The first grouping can include locations that are higher in the sequential order than locations in the second grouping. In such embodiments, the computing system 100 can discard (i) the locations included in the second grouping and (ii) locations included in groupings, if any, that are less diagnostically relevant than the second natural grouping. In some embodiments, the groups are discovered through the application of threshold values or ranges of values. In other embodiments, the groups are discovered "naturally," in the sense that the values output by the clustering algorithm may cluster together, leaving a gap or distance between the first and second groups. As another example, the computing system 100 may arrange, based on the set of relevance metrics, the locations included in the first set in sequential order from most diagnostically relevant to least diagnostically relevant and then discard the locations whose relevance metrics do not exceed a predetermined threshold. As another example, the computing system 100 may arrange, based on the set of relevance metrics, the locations included in the first set in sequential order from most diagnostically relevant to least diagnostically relevant, identify a highest N number of the locations based on an analysis of the sequential order, and then discard the locations that are not part of the highest N number. Regardless of the approach employed, the less diagnostically relevant locations may be discarded in such a way that accuracy of predictions is minimally impacted or not impacted.

At block 1212, the computing system 100 can provide the second set to the machine learning algorithm as input, so as to produce a trained ML model. As discussed above, the computing system 100 may store the trained ML model in a data structure that is associated with the given type of cancer, such that the trained ML model can be subsequently applied to genetic information of a patient whose health state is unknown for diagnostic purposes.

Figure 13:
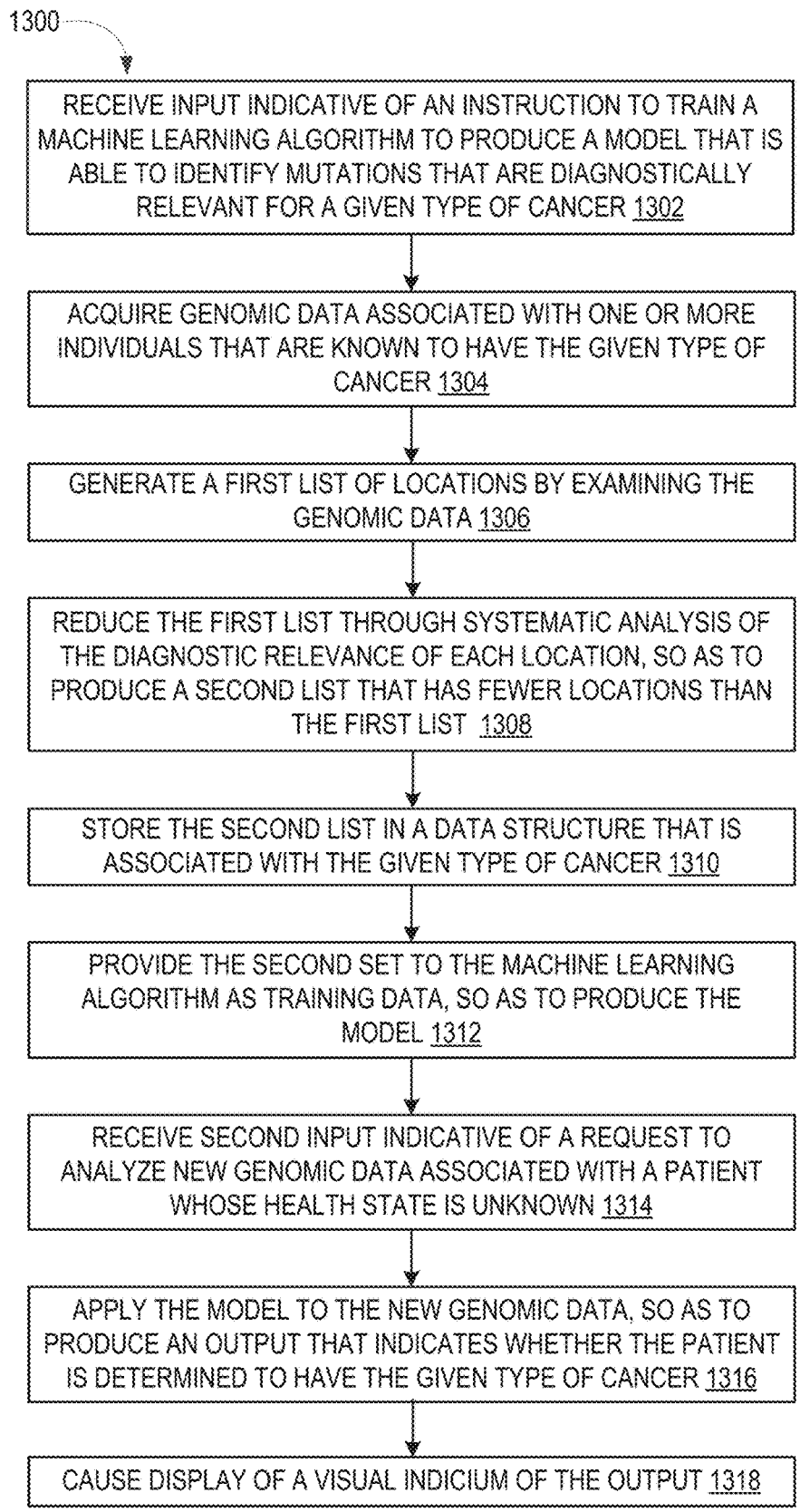
FIG. 13 includes a flow chart of a method for producing a filtered set of features for training of an ML model through systematic analysis of the diagnostic relevance of each of the features in accordance with one or more implementations of the present technology.

FIG. 13 includes a flow chart of a method 1300 for producing a filtered set of features for training of an ML model through systematic analysis of the diagnostic relevance of each of the features. At block 1302, the computing system 100 can receive input indicative of an instruction to train an ML algorithm to produce an ML model that is able to identify mutations that are diagnostically relevant for a given type of cancer. At block 1304, the computing system 100 can acquire genomic data that is associated with one or more individuals that are known to have the given type of cancer. For example, the computing system 100 may download the genomic data from a repository that is manipulable or interactable via a data portal accessible via the Internet. As a specific example, the repository may be associated with the National Cancer Institute, and the genomic data may be representative of a TCGA dataset. Note that, in some embodiments, the genomic data is associated with a single patient that is known to have the given type of cancer, while in other embodiments, the genomic data is associated with multiple patients that are known to have the given type of cancer.

At block 1306, the computing system 100 can generate a first list of locations by examining the genomic data. Each location included in the first list may be representative of a different molecular position at which a mutation is discovered through analysis of the genomic data. Block 1306 of FIG. 13 may be comparable to block 1206 of FIG. 12. At block 1308, the computing system 100 can reduce the first list through systematic analysis of the diagnostic relevance of each location, so as to produce a second list that has fewer locations than the first list. Various approaches to filtering or discarding less diagnostically relevant locations are described above. As part of its systematic analysis, the computing system 100 can determine the diagnostic relevance of each location included in the first list separately and then determine the diagnostic relevance of different combinations of locations included in the first list. For example, the computing system 100 may determine the diagnostic relevance of locations in the first list in an exhaustive, combinatorial manner. With this approach, the computing system 100 may discover that a combination of a first location and a second location are highly predictive of cancer, even though the first location is not highly predictive of cancer on its own and the second location is not highly predictive of cancer on its own. At a high level, this approach to systematically analyzing the diagnostic relevance may be helpful in establishing where accuracy in making accurate predictions (e.g., positive diagnoses of cancer) drops, for example, beneath a threshold.

At block 1310, the computing system 100 can store the second list in a data structure that is associated with the given type of cancer. For example, the computing system 100 may store the second list in a digital profile that is maintained for the given type of cancer. Additionally or alternatively, the computing system 100 may associate the second list with the given type of cancer, for example, by appending metadata that specifies the given type of cancer to the data structure.

As mentioned above, the second list could be used for training. Thus, the computing system 100 may provide the second list to the ML algorithm as training data, so as to produce the model as shown in block 1312. Upon being applied to new genomic data associated with a patient whose health state is unknown, the model can utilize the locations included in the second list to determine whether any mutations are present that are indicative of the given type of cancer. For example, the computing system 100 can receive second input indicative of a request to analyze new genomic data associated with a patient whose health state is unknown, as shown in block 1314. At block 1316, the computing system 100 applies the model to the new genomic data, so as to produce an output that indicates whether the patient is determined to have the given type of cancer, and at block 1318, the computing system 100 can cause display of a visual indicium of the output. For example, the computing system 100 may present the output itself or a visual representation of the output, such as a graphic (e.g., a chart) showing the likelihood of a positive diagnosis for the given type of cancer.

Figure 14:
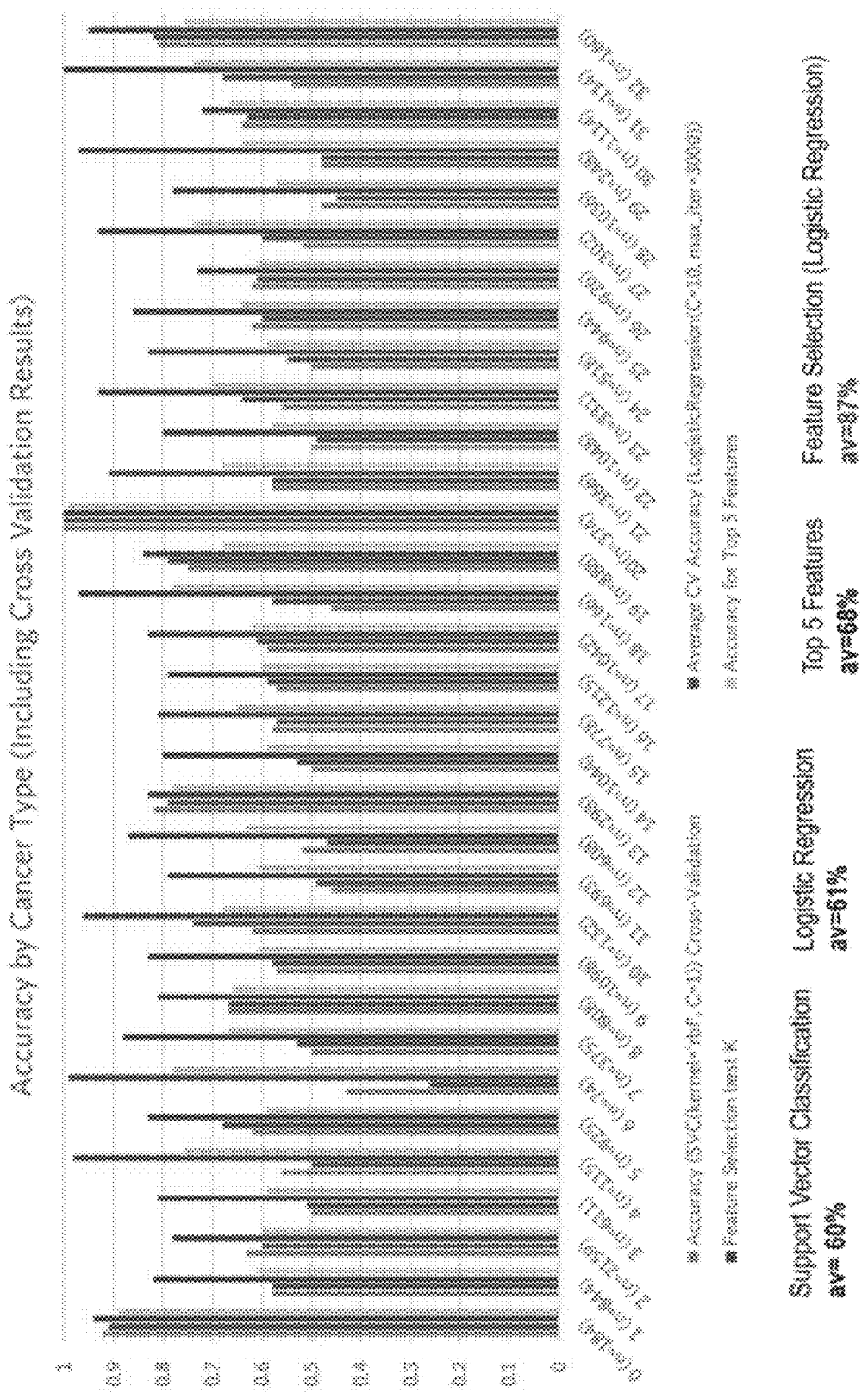
FIG. 14 includes a chart illustrating the accuracy of logistic regression with cross-validation to discriminate cancerous samples from healthy samples with the selection of optimal features for each of 33 different cancer types.

FIG. 14 includes a chart illustrating the accuracy of logistic regression with cross-validation to discriminate cancerous samples from healthy samples with the selection of optimal features for each of 33 different cancer types for which DNA data is available from TCGA. While these results are shown for logistic regression, those skilled in the art will recognize that other ML algorithms could be used instead of logistic regression. In FIG. 14, each cancer type is rated across four metrics, namely, (i) accuracy with cross-validation, (ii) average cross-validation accuracy, (iii) feature selection with optimal k, and (iv) accuracy for top five features. As can be seen in FIG. 14, feature selection with optimal k generally outperforms the alternative approaches.

Computing System

Figure 15:
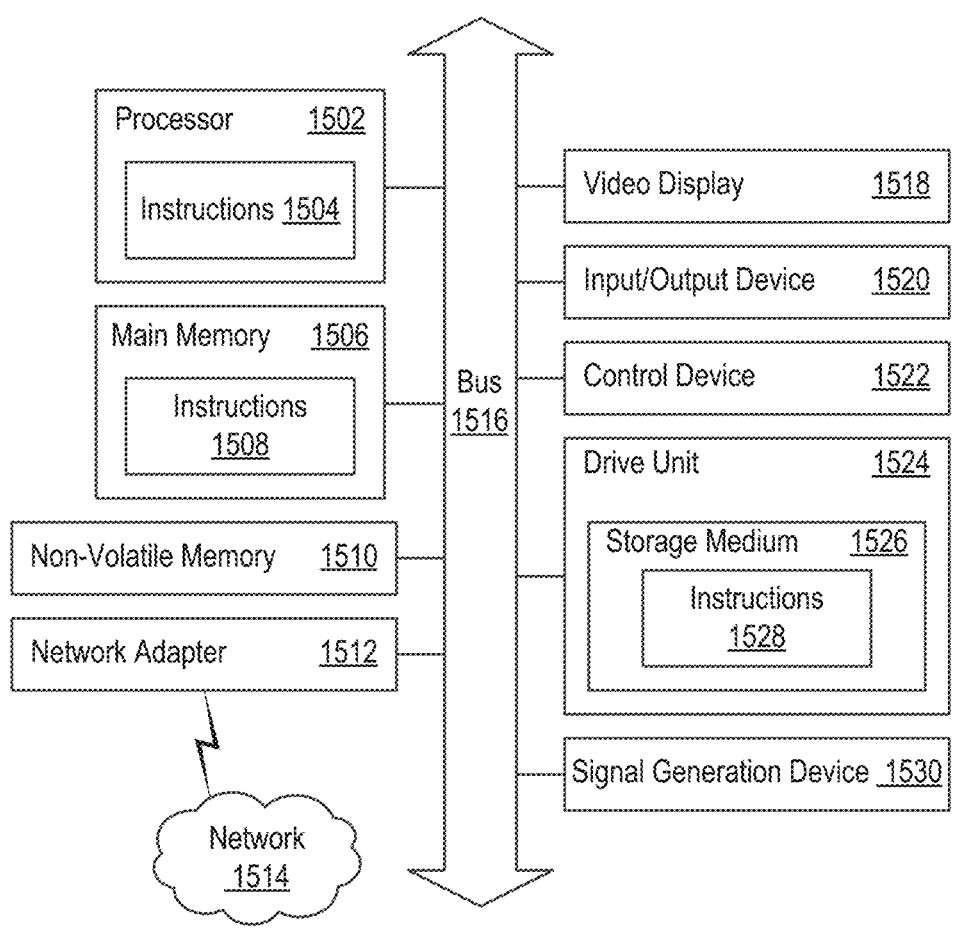
FIG. 15 is a block diagram illustrating an example of a computing system in accordance with one or more implementations of the present technology.

FIG. 15 is a block diagram illustrating an example of a computing system 1500 (e.g., the computing system 100 or a portion thereof, such as the processing system 102) in accordance with one or more implementations of the present technology. For example, some components of the system 1500 may be hosted on a computing device that includes a mutation analysis mechanism and a refinement mechanism.

The computing system 1500 may include a processor 1502, main memory 1506, non-volatile memory 1510, network adapter 1512, video display 1518, input/output device 1520, control device 1522 (e.g., a keyboard or pointing device), drive unit 1524 including a storage medium 1526, and signal generation device 1530 that are communicatively connected to a bus 1516. The bus 1516 is illustrated as an abstraction that represents one or more physical buses or point-to-point connections that are connected by appropriate bridges, adapters, or controllers. The bus 1516, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), inter-integrated circuit (I2C) bus, or an Institute of Electrical and Electronics Engineers (IEEE) standard 1394 bus (also referred to as "Firewire").

While the main memory 1506, non-volatile memory 1510, and storage medium 1526 are shown to be a single medium, the terms "machine-readable medium" and "storage medium" should be taken to include a single medium or multiple media (e.g., a centralized/distributed database and/or associated caches and servers) that store one or more sets of instructions 1528. The terms "machine-readable medium" and "storage medium" shall also be taken to include any medium that is capable of storing, encoding, or carrying a set of instructions for execution by the computing system 1500.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1504, 1508, 1528) set at various times in various memory and storage devices in a computing device. When read and executed by the processors 1502, the instruction(s) cause the computing system 1500 to perform operations to execute elements involving the various aspects of the present disclosure.

Further examples of machine- and computer-readable media include recordable-type media, such as volatile memory devices and non-volatile memory devices 1510, removable disks, hard disk drives, and optical disks (e.g., Compact Disk Read-Only Memory (CD-ROMS) and Digital Versatile Disks (DVDs)), and transmission-type media, such as digital and analog communication links.

The network adapter 1512 enables the computing system 1500 to mediate data in a network 1514 with an entity that is external to the computing system 1500 (e.g., between the processing system 102 and the sourcing device 152) through any communication protocol supported by the computing system 1500 and the external entity. The network adapter 1512 can include a network adaptor card, a wireless network interface card, a router, an access point, a wireless router, a switch, a multilayer switch, a protocol converter, a gateway, a bridge, bridge router, a hub, a digital media receiver, a repeater, or any combination thereof.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method comprising:

receiving an input indicative of an instruction to train a neural network to identify text phrases that are representative of mutations that are diagnostically relevant for a given type of cancer,
wherein each of the text phrases is representative of a different set of characters, each of which is representative of a nucleotide;

accessing a dataset that includes genetic information of multiple individuals that are known to have the given type of cancer;

generating a first set of locations by examining the dataset,
wherein each of the locations included in the first set is representative of a different molecular position at which a mutation is discovered through analysis of the genetic information;

producing a set of metrics by computing, for each of the locations included in the first set, a metric that is indicative of correlation with the given type of cancer, as determined based on an analysis of the genetic information of the multiple individuals;

generating a second set that includes fewer locations than the first set by
identifying the locations included in the first set in order based on the set of metrics, ordered from most correlated with the given type of cancer to least correlated with the given type of cancer, and
filtering at least some of the locations included in the first set, so as to produce the second set; and training the neural network using the second set.

2. The method of claim 1, wherein generating of the second set further comprises:
implementing a clustering algorithm to discover groupings of the locations,
identifying a first grouping and a second grouping that are separated by at least a predetermined amount,
wherein the first grouping includes locations that are higher in the order than locations in the second grouping, and
discarding (i) the locations included in the second grouping and (ii) locations included in groupings, if any, that correlate with the given type of cancer less than the second grouping.

3. The method of claim 1, wherein said generating of the second set comprises:
discarding the locations whose relevance metrics do not exceed a threshold.

4. The method of claim 1, wherein said generating of the second set comprises:
identifying a highest N number of the locations based on an analysis of the order, and
discarding the locations that are not part of the highest N number.

5. The method of claim 1, wherein said producing comprises:
for each of the locations,
outputting a score indicative of importance in producing a diagnostically accurate output.

6. The method of claim 5, wherein each score is representative of the metric produced for the corresponding location.

7. The method of claim 5, wherein said producing further comprises:
for each of the locations,
determining the corresponding metric based on the corresponding score output by the neural network.

8. The method of claim 5, wherein the score is indicative of accuracy, precision, recall, sensitivity, specificity, or localization.

9. The method of claim 1, wherein said producing comprises:
for each of the locations,
outputting multiple scores that are indicative of different performance metrics, and
determining the corresponding metric based on the multiple scores.

10. The method of claim 1, further comprising:
initiating a connection with a network-accessible source of genomic data; and causing the dataset to be downloaded from the network-accessible source.

11. The method of claim 10, wherein said initiating and said causing are performed in response to said receiving.

12. A non-transitory medium with instructions stored thereon that, when executed by a processor of a computing device, cause the computing device to perform operations comprising:
- receiving input indicative of an instruction to train a machine learning (ML) algorithm to produce a model that is able to identify mutations that are indicative of a given type of cancer;
- accessing genomic data associated with one or more individuals that are known to have the given type of cancer;
- generating a first list of locations by examining the genomic data,
   - wherein each location included in the first list is representative of a different molecular position at which a mutation is discovered through analysis of the genomic data;
- reducing the first list through systematic analysis of correlation of each location with the given type of cancer, as determined based on an analysis of the genomic data, so as to produce a second list that has fewer locations than the first list; and
- storing the second list in a data structure that is associated with the given type of cancer.

13. The non-transitory medium of claim 12, wherein the genomic data is associated with a single patient that is known to have the given type of cancer.

14. The non-transitory medium of claim 12, wherein the genomic data is associated with multiple patients that are known to have the given type of cancer.

15. The non-transitory medium of claim 12, wherein the operations further comprise:
- downloading the genomic data from a repository that is manipulable via a data portal accessible via the Internet.

16. The non-transitory medium of claim 15, wherein the repository is associated with the National Cancer Institute, and wherein the genomic data is representative of a The Cancer Genome Atlas (TCGA) dataset.

17. The non-transitory medium of claim 12, wherein the operations further comprise:
- training the ML algorithm using the second set, so as to produce the model.

18. The non-transitory medium of claim 17, wherein upon being applied to new genomic data associated with a patient whose health state is unknown, the model utilizes the locations included in the second list to determine whether any mutations are present that are indicative of the given type of cancer.

19. The non-transitory medium of claim 17, wherein the operations further comprise:
- receiving second input indicative of request to analyze new genomic data associated with a patient whose health state is unknown;
- applying the model to the new genomic data, so as to produce an output that indicates whether the patient is determined to have the given type of cancer; and
- causing display of a visual indicium of the output.

* * * * *